United States Patent [19]
Podsakoff et al.

[11] Patent Number: 5,962,313
[45] Date of Patent: *Oct. 5, 1999

[54] ADENO-ASSOCIATED VIRUS VECTORS COMPRISING A GENE ENCODING A LYOSOMAL ENZYME

[75] Inventors: Gregory M. Podsakoff, Fullerton, Calif.; Paul D. Kessler; Barry J. Byrne, both of Baltimore, Md.; Gary J. Kurtzman, Menlo Park, Calif.

[73] Assignees: Avigen, Inc., Alameda, Calif.; Johns Hopkins University, Baltimore, Md.

[ * ] Notice: This patent is subject to a terminal disclaimer.

[21] Appl. No.: 08/784,757

[22] Filed: Jan. 16, 1997

Related U.S. Application Data

[63] Continuation-in-part of application No. 08/588,355, Jan. 18, 1996.
[51] Int. Cl.$^6$ .............................. C12N 15/00; A61K 48/00
[52] U.S. Cl. .......................... 435/320.1; 435/455; 514/44
[58] Field of Search ................................ 424/93.2, 93.21; 514/44; 435/320; 536/23.1, 24.1

[56] References Cited

U.S. PATENT DOCUMENTS

| | | |
|---|---|---|
| 5,252,479 | 10/1993 | Srivastava . |
| 5,589,362 | 12/1996 | Bujard et al. . |
| 5,658,565 | 8/1997 | Billiar et al. .......................... 424/93.21 |

FOREIGN PATENT DOCUMENTS

| | | |
|---|---|---|
| WO 94/13788 | 6/1994 | WIPO . |
| WO 95/13376 | 5/1995 | WIPO . |
| WO 95/20671 | 8/1995 | WIPO . |
| WO 95/34670 | 12/1995 | WIPO . |
| WO 96/40272 | 12/1996 | WIPO . |

OTHER PUBLICATIONS

Tzail et al (1991) Biochem. Biophys. Res. Comm. 176, 1509–15–15.
Stratford–Pemcaudet et al (1992) J. Clin. Invest. 90, 626–630.
Blau et al., "Myoblast in Pattern Formation and Gene Therapy," *Trends In Genetics* 9(8):269–274(1993).
Clark et al., "Cell Lines for the Production of Recombinant Adeno–Associated Virus," *Human Gene Therapy* 6:1329–1341(1995).
Kourtis et al., "Cardiac Gene Therapy with Adeno–Associated Virus as a Means of Achieving Graft–Specific Immunosuppression," *Modern Pathology* 8(1):33A(178)(1995).
Podsakoff et al., "Long–Term In Vivo Gene Expression in Muscle Using AAV Vectors," *J. of The American Society of Hematology* 86(10):1004A(4004)(1995).
Tripathy et al., "Stable Delivery of Physiologic Levels of Recombinant Erythropoietin to the Systemic Circulation by Intramuscular Injection of Replication–Defective Adenovirus," *Proc. Natl. Acac. Sci. USA* 91:11557–11561(1994).
Kessler et al., "Gene Delivery to Skeletal Muscle Results in Sustained Expression and Systemic Delivery of a Therapeutic Protein," *Proc. Natl. Acad. Sci. USA* 93:14082–14087 (1996).

Naffakh et al., "Long–Term Secretion of Therapeutic Proteins from Genetically Modified Skeletal Muscles," *Human Gene Therapy* 7:11–21 (1996).
Podsakoff et al., "AAV Vector–Mediated Gene Delivery to Skeletal Muscle In Vivo Results in Sustained Levels of Systemic Erythropoietin," *Blood* 88(10):1066(1996).
Acsadi et al., "Human dystrophin expression in mdx mice after intramuscular injection of DNA constructs," *Nature* (1991) 352:815–818.
Acsadi et al., "Cultured human myoblasts and myotubes show markedly different transducibility by replication–defective adenovirus recombinants," *Gene Therapy* (1994) 1:338–340.
Acsadi et al., "A differential efficiency of adenovirus–mediated in vivo gene transfer into skeletal muscle cells of different maturity," *Hum. Mol. Genetics* (1994)3:579–584.
Barr and Leiden, "Systemic delivery of recombinant proteins by genetically modified myoblasts," *Science* (1991) 254:1507–1509.
Bartlett et al., *Am. J. Human Genetics* (1995) 57 (Supp 4) #A235.
Blau and Springer, "Molecular medicine muscle–mediated gene therapy," *New Eng. J. Med.* (1995)333:1204–1207.
Blau and Springer, "Molecular medicine gene therapy—a novel form of drug delivery," *New Eng. J. Med.* (1995)333:1554–1556.
Dai et al., "Gene therapy via primary myoblasts: long–term expression of factor IX protein following transplantation in vitro," *Proc. Natl. Acad. Sci. USA* (1992) 89:10892–10895.
Dai et al., "Cellular and humoral immune responses to adenoviral vectors containing factor IX gene: tolerization of factor IX and vector antigens allows for long–term expression," *Proc. Natl. Acad. Sci. USA* (1995) 92:1401–1405.
Davis et al., "Direct gene transfer into skeletal muscle in vivo: Factors affecting efficiency of transfer and stability of expression," *Hum. Gene Therapy* (1993) 4:151–159.
Descamps et al., "Organoids direct systemic expression of erythropoietin in mice," *Gene Therapy* (1995) 2:411–417.
Dhawan et al., "Systemic delivery of human growth hormone by injection of genetically engineered myoblasts," *Science* (1991) 254:1509–1512.

(List continued on next page.)

*Primary Examiner*—Deborah Crouch
*Attorney, Agent, or Firm*—Robins & Associates

[57] ABSTRACT

The use of recombinant adeno-associated virus (AAV) virions for delivery of DNA molecules to muscle cells and tissue is disclosed. The invention allows for the direct, in vivo injection of recombinant AAV virions into muscle tissue, e.g., by intramuscular injection, as well as for the in vitro transduction of muscle cells which can subsequently be introduced into a subject for treatment. The invention provides for sustained, high-level expression of the delivered gene and for in vivo secretion of the therapeutic protein from transduced muscle cells such that systemic delivery is achieved.

6 Claims, 8 Drawing Sheets

OTHER PUBLICATIONS

Einerhand et al., "Regulated high–level human β–globin gene expression in erythroid cells following recombinant adeno–associated virus–mediated gene transfer," *Gene Therapy* (1995) 2:336–343.

Flotte et al., "Gene expression from Adeno–associated virus vectors in airway epithelial cells," *Am. J. Respir. Cell Mol. Biol.* (1992) 7:349–356.

Flotte et al., "Expression of the cystic fibrosis transmembrane conductance regulator from a novel adeno–associated virus promoter," *J. Biol. Chem.* (1993) 268:3781–3790.

Flotte et al., "Stable in vivo expression of the cystic fibrosis transmembrane conductance regulator with an adeno–associated virus vector," *Proc. Natl. Acad. Sci. USA* (1993) 90:10613–10617.

Flotte et al., "Adeno–associated virus vector gene expression occurs in nondividing cells in the absence of vector DNA integration," *Am. J. Respir. Cell Mol. Biol.* (1994) 11:517–521.

Gilgenkrantz et al., "Transient expression of genes transferred in vivo into heart using first–generation adenoviral vectors: role of the immune response," *Hum. Gene Therapy* (1995) 6:1265–1274.

Hamamori et al., "Persistent erythropoiesis by myoblast transfer of erythropoietin cDNA," *Hum. Gene Therapy* (1994) 5:1349–1356.

Hamamori et al., "Myoblast transfer of human erythropoietin gene in a mouse model of renal failure," *J. Clin. Invest.* (1995) 95:1808–1813.

Kaplitt et al., "Long–term gene expression and phenotypic correction using adeno–associated virus vectors in the mammalian brain," *Nature Genetics* (1994) 8:148–154.

Knowles et al., "A controlled study of adenoviral–vector-–mediated gene transfer in the nasal epithelium of patients with cystic fibrosis," *The New Eng. J. of Med.* (1995) 333(13):823–831.

Leiden, "Gene therapy–promise, pitfalls and prognosis," *New Eng. J. Med.* (1995) 333:871–872.

March et al., *Clin. Res.* (1992) 40(2):358A.

Mendell et al., "Myoblast transfer in the treatment of Duchenne's muscular dystrophy," *New Eng. J. Med.* (1995) 333:832–838.

Naffakh et al., "Sustained delivery of erythropoietin in mice by genetically modified skin fibroblasts," *Proc. Natl. Acad. Sci.* (1995) 92:3194–3198.

Osborne et al., "Gene therapy for long–term expression of erythropoietin in rats," *Proc. Natl. Acad. Sci.* (1995) 92:8055–8058.

Podsakoff et al., "Efficient gene–transfer into nondividing cells by adeno–associated virus–based vectors," *J. Virol.* (1994) 68:5656–5666.

Quantin et al., "Adenovirus as an expression vector in muscle cells in vivo," *Proc. Natl. Acad. Sci. USA* (1992) 89:2581–2584.

Raz et al., "Systemic immunological effects of cytokine genes injected into skeletal muscle," *Proc. Natl. Acad. Sci. USA* (1993) 90:4523–4527.

Russell et al., "Adeno–associated virus vectors preferentially transduce cells in S phase," *Proc. Natl. Sci. USA* (1994) 91:8915–8919.

Villeval et al., "Retrovirus–medicated transfer of the erythropoietin gene in hematopoietic cells improves the erythrocyte phenotype in murine β–thalassemia," *Blood* (1994) 84(3):928–933.

Wolff et al., "Direct gene transfer into mouse muscle in vivo," *Science* (1990) 247:1465–1468.

Wolff et al., "Long–term persistence of plasmid DNA and foreign gene expression in mouse muscle," *Human Mol. Genet.* (1992) 1:363–369.

Xiao et al., "Adeno–associated virus (AAV) vectors for gene transfer," *Advanced Drug Delivery Reviews* (1993) 12:201–215.

Xiao et al., "Efficient long–term gene transfer into Muscle tissue of immunocompetent mice by adeno–addociated virus vector," *J. of Virol.* (1996) 70(11):8098–8108.

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GGCAGCTGCC TGCA                                    14

(2) INFORMATION FOR SEQ ID NO:2:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

GAAGGCGCGC CTTC                                    14

(2) INFORMATION FOR SEQ ID NO:3:

(i) SEQUENCE CHARACTERISTICS:
      (A) LENGTH: 80 base pairs
      (B) TYPE: nucleic acid
      (C) STRANDEDNESS: single (D) TOPOLOGY: linear (ii) MOLECULE TYPE: DNA (genomic)

(xi) SEQUENCE DESCRIPTION: SEQ ID NO:3:

GCGGCCGCAC GCGTACGTAC CGGTTCGAAG CGCGCACGGC CGACCATGGT TAACTCCGGA     60

CACGTGCGGA CCGCGGCCGC                                                80

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AAAATTCGAA CCTGGGGAGA AACCAGAG                                       28

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GTTTCCCCGC GAATGGACAA GCTTAAAA                                       28

(2) INFORMATION FOR SEQ ID NO:6:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCGGCCGCAC GCGTTGTTAA CAACCGGTTC GAAGCGCGCA GCGGCCGACC ATGGGTTTAA     60

ACTCCGGACC ACGTGCGGAC CGAGCGGCCG C                                   91

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AAAATTCGAA CAGGTAAGCG CCCCTTTG                                       28

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GAGACCAAAG AGGGGTCCAA GCTTAAAA                                           28

(2) INFORMATION FOR SEQ ID NO:9:

(i) SEQUENCE CHARACTERISTICS:
            (A) LENGTH: 101 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

GAGCTCAATC GATTGAATTC CCCGGGGATC CTCTAGAGTC GACCTGCAGC CACTGTGTTG        60

GATATCCAAC ACACTGGTAG GGATAACAGG GTAATCTCGA G                           101

ADENO-ASSOCIATED VIRUS VECTORS COMPRISING A GENE ENCODING A LYOSOMAL ENZYME

CROSS-REFERENCE TO RELATED APPLICATION

This application is a continuation-in-part of U.S. application Serial No. 08/588,355, filed Jan. 18, 1996, from which priority is claimed pursuant to 35 USC §120 and which is incorporated herein by reference in its entirety.

TECHNICAL FIELD

The present invention relates generally to DNA delivery methods. More particularly, the invention relates to the use of recombinant adeno-associated virus (AAV) virions for delivery of a selected gene to muscle cells and tissue. The method provides for sustained, high-level expression of the delivered gene.

BACKGROUND OF THE INVENTION

Gene delivery is a promising method for the treatment of acquired and inherited diseases. Muscle tissue is an appealing gene delivery target because it is readily accessible, well-differentiated and nondividing. Barr and Leiden (1991) *Science* 254:1507–1509. These properties are important in the selection of appropriate delivery strategies to achieve maximal gene transfer.

Several experimenters have demonstrated the ability to deliver genes to muscle cells with the subsequent systemic circulation of proteins encoded by the delivered genes. See, e.g., Wolff et al. (1990) *Science* 247:1465–1468; Acsadi et al. (1991) *Nature* 352:815–818; Barr and Leiden (1991) *Science* 254:1507–1509; Dhawan et al. (1991) *Science* 254:1509–1512; Wolff et al. (1992) *Human Mol. Genet.* 1:363–369; Eyal et al. (1993) *Proc. Natl. Acad. Sci. USA* 90:4523–4527; Davis et al. (1993) *Hum. Gene Therapy* 4:151–159.

Genes have been delivered to muscle by direct injection of plasmid DNA, such as described by Wolff et al. (1990) *Science* 247:1465–1468; Acsadi et al. (1991) *Nature* 352:815–818; Barr and Leiden (1991) *Science* 254:1507–1509. However, this mode of administration generally results in sustained but low levels of expression. Low but sustained expression levels may be effective in certain situations, such as for providing immunity.

Viral based systems have also been used for gene delivery to muscle. For example, human adenoviruses are double-stranded DNA viruses which enter cells by receptor-mediated endocytosis. These viruses have been considered well suited for gene transfer because they are easy to grow and manipulate and they exhibit a broad host range in vivo and in vitro. Adenoviruses are able to infect quiescent as well as replicating target cells and persist extrachromosomally, rather than integrating into the host genome.

Despite these advantages, adenovirus vectors suffer from several drawbacks which make them ineffective for long term gene therapy. In particular, adenovirus vectors express viral proteins that may elicit an immune response which may decrease the life of the transduced cell. This immune reaction may preclude subsequent treatments because of humoral and/or T cell responses. Furthermore, the adult muscle cell may lack the receptor which recognizes adenovirus vectors, precluding efficient transduction of this cell type using such vectors. Thus, attempts to use adenoviral vectors for the delivery of genes to muscle cells has resulted in poor and/or transitory expression. See, e.g., Quantin et al. (1992) *Proc. Natl. Acad. Sci. USA* 89:2581–2584; Acsadi et al. (1994) *Hum. Mol. Genetics* 3:579–584; Acsadi et al. (1994) *Gene Therapy* 1:338–340; Dai et al. (1995) *Proc. Natl. Acad. Sci. USA* 92:1401–1405; Descamps et al. (1995) *Gene Therapy* 2:411–417; Gilgenkrantz et al. (1995) *Hum. Gene Therapy* 6:1265–1274.

Gene therapy methods based upon surgical transplantation of myoblasts has also been attempted. See, e.g., International Publication no. WO 95/13376; Dhawan et al. (1991) *Science* 254:1509–1512; Wolff et al. (1992) *Human Mol. Genet.* 1:363–369; Dai et al. (1992) *Proc. Natl. Acad. Sci. USA* 89:10892–10895; Hamamori et al. (1994) *Hum. Gene Therapy* 5:1349–1356; Hamamori et al. (1995) *J. Clin. Invest.* 95:1808–1813; Blau and Springer (1995) *New Eng. J. Med.* 333:1204–1207; Leiden, J. M. (1995) *New Eng. J. Med.* 333:871–872; Mendell et al. (1995) *New Eng. J. Med.* 333:832–838; and Blau and Springer (1995) *New Eng. J. Med.* 333:1554–1556. However, such methods require substantial tissue culture manipulation and surgical expertise, and, at best, show inconclusive efficacy in clinical trials. Thus, a simple and effective method of gene delivery to muscle, resulting in long-term expression of the delivered gene, would be desirable.

Recombinant vectors derived from an adeno-associated virus (AAV) have been used for gene delivery. AAV is a helper-dependent DNA parvovirus which belongs to the genus Dependovirus. AAV requires infection with an unrelated helper virus, such as adenovirus, a herpesvirus or vaccinia, in order for a productive infection to occur. The helper virus supplies accessory functions that are necessary for most steps in AAV replication. In the absence of such infection, AAV establishes a latent state by insertion of its genome into a host cell chromosome. Subsequent infection by a helper virus rescues the integrated copy which can then replicate to produce infectious viral progeny. AAV has a wide host range and is able to replicate in cells from any species so long as there is also a successful infection of such cells with a suitable helper virus. Thus, for example, human AAV will replicate in canine cells coinfected with a canine adenovirus. AAV has not been associated with any human or animal disease and does not appear to alter the biological properties of the host cell upon integration. For a review of AAV, see, e.g., Berns and Bohenzky (1987) *Advances in Virus Research* (Academic Press, Inc.) 32:243–307.

The AAV genome is composed of a linear, single-stranded DNA molecule which contains approximately 4681 bases (Berns and Bohenzky, supra). The genome includes inverted terminal repeats (ITRs) at each end which function in cis as origins of DNA replication and as packaging signals for the virus. The internal nonrepeated portion of the genome includes two large open reading frames, known as the AAV rep and cap regions, respectively. These regions code for the viral proteins involved in replication and packaging of the virion. For a detailed description of the AAV genome, see, e.g., Muzyczka, N. (1992) *Current Topics in Microbiol. and Immunol.* 158:97–129.

The construction of recombinant AAV (rAAV) virions has been described. See, e.g., U.S. Pat. Nos. 5,173,414 and 5,139,941; International Publication Numbers WO 92/01070 (published Jan. 23, 1992) and WO 93/03769 (published Mar. 4, 1993); Lebkowski et al. (1988) *Molec. Cell. Biol.* 8:3988–3996; Vincent et al. (1990) *Vaccines 90* (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; and Kotin, R. M. (1994) *Human Gene Therapy* 5:793–801.

Recombinant AAV virion production generally involves cotransfection of a producer cell with an AAV vector plasmid and a helper construct which provides AAV helper functions to complement functions missing from the AAV vector plasmid. In this manner, the producer cell is capable of expressing the AAV proteins necessary for AAV replication and packaging. The AAV vector plasmid will include the DNA of interest flanked by AAV ITRs which provide for AAV replication and packaging functions. AAV helper functions can be provided via an AAV helper plasmid that includes the AAV rep and/or cap coding regions but which lacks the AAV ITRs. Accordingly, the helper plasmid can neither replicate nor package itself. The producer cell is then infected with a helper virus to provide accessory functions, or with a vector which includes the necessary accessory functions. The helper virus transactivates the AAV promoters present on the helper plasmid that direct the transcription and translation of AAV rep and cap regions. Upon subsequent culture of the producer cells, recombinant AAV virions harboring the DNA of interest, are produced.

Recombinant AAV virions have been shown to exhibit tropism for respiratory epithelial cells (Flotte et al. (1992) *Am. J. Respir. Cell Mol. Biol.* 7:349–356; Flotte et al. (1993) *J. Biol. Chem.* 268:3781–3790; Flotte et al. (1993) *Proc. Natl. Acad. Sci. USA* 90:10613–10617) and neurons of the central nervous system (Kaplitt et al. (1994) *Nature Genetics* 8:148–154). These cell types are well-differentiated, slowly-dividing or postmitotic. Flotte et al. (1993) *Proc. Natl. Acad. Sci. USA* 90:10613–10617; Kaplitt et al. (1994) *Nature Genetics* 8:148–154. The ability of AAV vectors to transduce nonproliferating cells (Podsakoff et al. (1994) *J. Virol.* 68:5656–5666; Russell et al. (1994) *Proc. Natl. Acad. Sci. USA* 91:8915–8919; Flotte et al. (1994) *Am. J. Respir. Cell Mol. Biol.* 11:517–521) along with the attributes of being inherently defective and nonpathogenic, place AAV in a unique position among gene therapy viral vectors.

Despite these advantages, the use of recombinant AAV virions to deliver genes to muscle cells in vivo has not heretofore been disclosed.

SUMMARY OF THE INVENTION

Accordingly, the present invention is based on the surprising and unexpected discovery that recombinant AAV (rAAV) virions provide for efficient delivery of genes and sustained production of therapeutic proteins in various muscle cell types. The invention allows for in vivo secretion of the therapeutic protein from transduced muscle cells such that systemic delivery of therapeutic levels of the protein is achieved. These results are seen with both in vivo and in vitro modes of DNA delivery. Hence, rAAV virions allow delivery of DNA directly to muscle tissue. The ability to deliver and express genes in muscle cells, as well as to provide for secretion of the produced protein from transduced cells, allows the use of gene therapy approaches to treat and/or prevent a wide variety of disorders.

Furthermore, the ability to deliver DNA to muscle cells by intramuscular administration in vivo provides a more efficient and convenient method of gene transfer.

Thus, in one embodiment, the invention relates to a method of delivering a selected gene to a muscle cell or tissue. The method comprises:

(a) providing a recombinant AAV virion which comprises an AAV vector, the AAV vector comprising the selected gene operably linked to control elements capable of directing the in vivo transcription and translation of the selected gene; and (b) introducing the recombinant AAV virion into the muscle cell or tissue.

In particularly preferred embodiments, the selected gene encodes a therapeutic protein, such as erythropoietin (EPO), or the lysosomal enzyme, acid α-glucosidase (GAA).

In another embodiment, the invention is directed to a muscle cell or tissue transduced with a recombinant AAV virion which comprises an AAV vector, the AAV vector comprising a selected gene operably linked to control elements capable of directing the in vivo transcription and translation of the selected gene.

In still further embodiments, the invention is directed to a method of treating an acquired or inherited disease in a mammalian subject comprising introducing into a muscle cell or tissue of the subject, in vivo, a therapeutically effective amount of a pharmaceutical composition which comprises (a) a pharmaceutically acceptable excipient; and (b) recombinant AAV virions. The recombinant AAV virions comprise an AAV vector, the AAV vector comprising a selected gene operably linked to control elements capable of directing the transcription and translation of the selected gene when present in the subject.

In yet another embodiment, the invention is directed to a method of treating an acquired or inherited disease in a mammalian subject comprising:

(a) introducing a recombinant AAV virion into a muscle cell or tissue in vitro to produce a transduced muscle cell. The recombinant AAV virion comprises an AAV vector, the AAV vector comprising a selected gene operably linked to control elements capable of directing the transcription and translation of the selected gene when present in the subject; and (b) administering to the subject a therapeutically effective amount of a composition comprising a pharmaceutically acceptable excipient and the transduced muscle cells from step (a).

In a further embodiment, the invention relates to a method for delivering a therapeutically effective amount of a protein systemically to a mammalian subject comprising introducing into a muscle cell or tissue of the subject a pharmaceutical composition which comprises (a) a pharmaceutically acceptable excipient; and (b) recombinant AAV virions, wherein the recombinant AAV virions comprise an AAV vector, the AAV vector comprising a selected gene operably linked to control elements capable of directing the transcription and translation of the selected gene when present in the subject, wherein the introducing is done in vivo.

In another embodiment, the invention is directed to a method for delivering a therapeutically effective amount of a protein systemically to a mammalian subject comprising:

(a) introducing a recombinant AAV virion into a muscle cell or tissue in vitro to produce a transduced muscle cell, wherein the recombinant AAV virion comprises an AAV vector, the AAV vector comprising a selected gene operably linked to control elements capable of directing the transcription and translation of the selected gene when present in the subject; and (b) administering to the subject a therapeutically effective amount of a composition comprising a pharmaceutically acceptable excipient and the transduced muscle cells from step (a).

In other embodiments, the invention is directed to an AAV vector comprising a gene encoding either erythropoietin (EPO), or acid α-glucosidase (GAA), operably linked to control elements capable of directing the in vivo transcription and translation of the gene, as well as a recombinant AAV (rAAV) virion comprising the vector.

These and other embodiments of the subject invention will readily occur to those of ordinary skill in the art in view of the disclosure herein.

DETAILED DESCRIPTION OF THE INVENTION

Figure 1A:
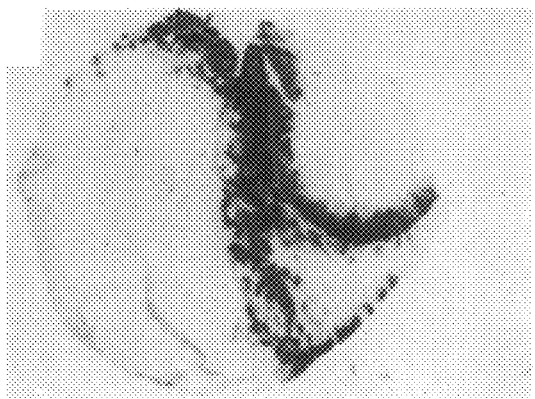
FIG. 1 shows in situ histochemical detection of β-galactosidase expression in murine muscle cells following transduction with rAAV-LacZ as described in Example 3, Part A. In the study, the tibialis anterior muscle of adult Balb/c mice was injected with $8 \times 10^9$ rAAV-LacZ. Animals were sacrificed (a) 2, (b) 4, (c) 8, (d) 12, (e) 24, of (f) 32 weeks after injection. The tibialis anterior was excised, and 10 mm sections were stained by X-gal for β-galactosidase histochemistry. The stained tissue samples were photographed at 25×.
Figure 1B:
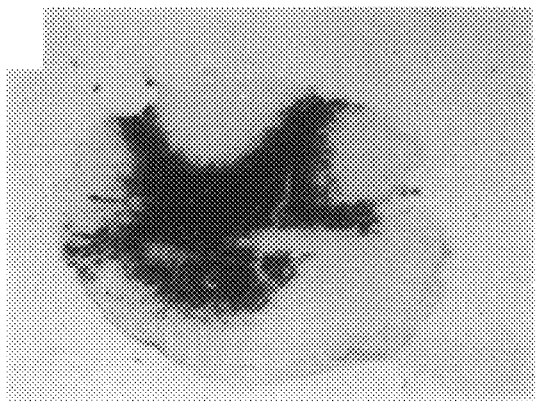
Figure 1C:
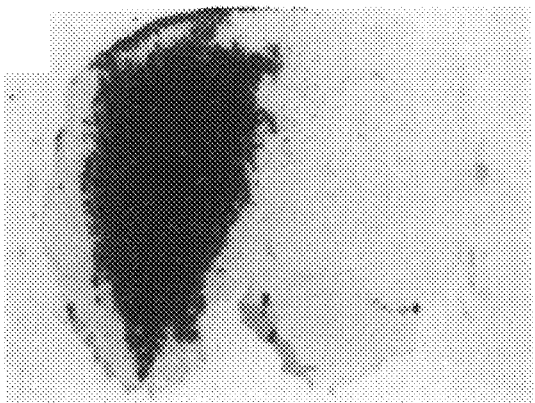
Figure 1D:
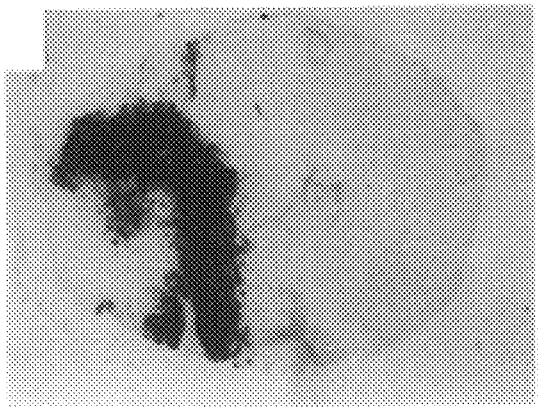
Figure 1E:
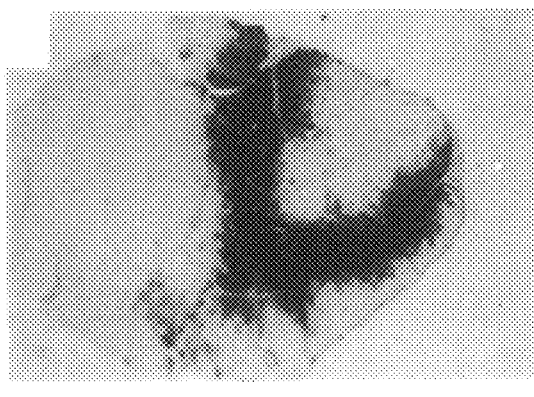
Figure 1F:
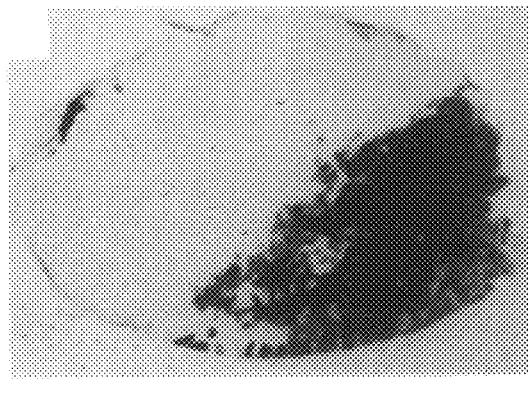

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijssen, ed.); *Fundamental Virology*, 2nd Edition, vol. I & II (B. N. Fields and D. M. Knipe, eds.)

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

The phrase "gene delivery" or "gene transfer" refers to methods or systems for reliably inserting foreign DNA into target cells, such as into muscle cells. Such methods can result in transient or long term expression of genes. Gene transfer provides a unique approach for the treatment of acquired and inherited diseases. A number of systems have been developed for gene transfer into mammalian cells. See, e.g., U.S. Pat. No. 5,399,346.

The term "therapeutic protein" refers to a protein which is defective or missing from the subject in question, thus resulting in a disease state or disorder in the subject, or to a protein which confers a benefit to the subject in question, such as an antiviral, antibacterial or antitumor function. A therapeutic protein can also be one which modifies any one of a wide variety of biological functions, such as endocrine, immunological and metabolic functions. Representative therapeutic proteins are discussed more fully below.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By "AAV vector" is meant a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes (described below), but retain functional flanking ITR sequences (also described below). Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

By "recombinant virus" is meant a virus that has been genetically altered, e.g., by the addition or insertion of a heterologous nucleic acid construct into the particle.

By "AAV virion" is meant a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

A "recombinant AAV virion," or "rAAV virion" is defined herein as an infectious, replication-defective virus composed of an AAV protein shell, encapsidating a DNA molecule of interest which is flanked on both sides by AAV ITRs. An rAAV virion is produced in a suitable producer cell which has had an AAV vector, AAV helper functions and accessory functions introduced therein. In this manner, the producer cell is rendered capable of encoding AAV polypeptides that are required for packaging the AAV vector (containing a recombinant nucleotide sequence of interest) into recombinant virion particles for subsequent gene delivery.

The term "transfection" is used to refer to the uptake of foreign DNA by a mammalian cell. A cell has been "transfected" when exogenous DNA has been introduced inside the cell membrane. A number of transfection techniques are known in the art. See, e.g., Graham et al. (1973) *Virology*, 52:456, Sambrook et al. (1989) *Molecular Cloning, a laboratory manual*, Cold Spring Harbor Laboratories, New York; Davis et al. (1986) Basic *Methods in Molecular Biology*, Elsevier, and Chu et al. (1981) *Gene* 13:197. Such techniques can be used to introduce one or more exogenous DNA moieties, such as a plasmid vector and other nucleic acid molecules, into suitable cells. The term refers to both stable and transient uptake of the genetic material.

The term "transduction" denotes the delivery of a DNA molecule to a recipient cell either in vivo or in vitro, via a replication-defective viral vector, such as via a recombinant AAV virion.

By "muscle cell" or "tissue" is meant a cell or group of cells derived from muscle, including but not limited to cells and tissue derived from skeletal muscle; smooth muscle, e.g., from the digestive tract, urinary bladder and blood vessels; and cardiac muscle. The term captures muscle cells both in vitro and in vivo. Thus, for example, an isolated cardiomyocyte would constitute a "muscle cell" for purposes of the present invention, as would a muscle cell as it exists in muscle tissue present in a subject in vivo. The term also encompasses both differentiated and nondifferentiated muscle cells, such as myocytes, myotubes, myoblasts, cardiomyocytes and cardiomyoblasts.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct in which the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

By "DNA" is meant a polymeric form of deoxyribonucleotides (adenine, guanine, thymine, or cytosine) in double-stranded or single-stranded form, either relaxed and super-coiled. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 31 direction along the nontranscribed strand of DNA (i.e., the strand having the sequence homologous to the mRNA). The term captures molecules that include the four bases adenine, guanine, thymine, or cytosine, as well as molecules that include base analogues which are known in the art.

A "gene" or "coding sequence" or a sequence which "encodes" a particular protein, is a nucleic acid molecule which is transcribed (in the case of DNA) and translated (in the case of mRNA) into a polypeptide in vitro or in vivo when placed under the control of appropriate regulatory sequences. The boundaries of the gene are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

"Homology" refers to the percent of identity between two polynucleotide or two polypeptide moieties. The correspondence between the sequence from one moiety to another can be determined by techniques known in the art. For example, homology can be determined by a direct If comparison of the sequence information between two polypeptide molecules by aligning the sequence information and using readily available computer programs. Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match using the methods above.

By "mammalian subject" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

B. General Methods

The present invention provides for the successful transfer of a selected gene to a muscle cell using recombinant AAV virions. The method allows for the direct, in vivo injection of recombinant AAV virions into muscle tissue, e.g., by intramuscular injection, as well as for the in vitro transduction of muscle cells which can subsequently be introduced into a subject for treatment. The invention also provides for secretion of the produced protein in vivo, from transduced muscle cells, such that systemic delivery can be achieved.

Muscle provides a desirable target for gene therapy since muscle cells are readily accessible and nondividing. However, the present invention also finds use with nondifferentiated muscle cells, such as myoblasts, which can be transduced in vitro, and subsequently introduced into a subject.

Since muscle has ready access to the circulatory system, a protein produced and secreted by muscle cells and tissue in vivo will enter the bloodstream for systemic delivery. Furthermore, since sustained, therapeutic levels of protein secretion from muscle is achieved in vivo using the present invention, repeated parenteral delivery is avoided or reduced in frequency such that therapy can be accomplished using only one or few injections. Thus, the present invention provides significant advantages over prior gene delivery methods.

The recombinant AAV virions of the present invention, including the DNA of interest, can be produced using standard methodology, known to those of skill in the art. The methods generally involve the steps of (1) introducing an AAV expression vector into a producer cell; (2) introducing an AAV helper construct into the producer cell, where the helper construct includes AAV coding regions capable of being expressed in the producer cell to complement AAV helper functions missing from the AAV vector; (3) introducing one or more helper viruses and/or accessory function vectors into the producer cell, wherein the helper virus and/or accessory function vectors provide accessory functions capable of supporting efficient recombinant AAV ("rAAV") virion production in the cell; and (4) culturing the producer cell to produce rAAV virions. The AAV expression vector, AAV helper construct and the helper virus or accessory function vector(s) can be introduced into the producer cell, either simultaneously or serially, using standard transfection techniques.

1. AAV Expression Vectors

AAV expression vectors are constructed using known techniques to at least provide as operatively linked components in the direction of transcription, control elements including a transcriptional initiation region, the DNA of interest and a transcriptional termination region. The control elements are selected to be functional in a mammalian muscle cell. The resulting construct which contains the operatively linked components is bounded (5' and 3') with functional AAV ITR sequences.

The nucleotide sequences of AAV ITR regions are known. See, e.g., Kotin, R. M. (1994) *Human Gene Therapy* 5:793–801; Berns, K. I. "Parvoviridae and their Replication" in *Fundamental Virology*, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV expression vector need not necessarily be identical or derived from the same AAV serotype or isolate, so long as they function as intended, i.e., to allow for packaging of virions.

Suitable DNA molecules for use in AAV vectors will be less than about 5 kilobases (kb) in size and will include, for example, a gene that encodes a protein that is defective or missing from a recipient subject or a gene that encodes a protein having a desired biological or therapeutic effect (e.g., an antibacterial, antiviral or antitumor function).

Suitable DNA molecules include, but are not limited to, those encoding for proteins used for the treatment of endocrine, metabolic, hematologic, cardiovascular, neurologic, musculoskeletal, urologic, pulmonary and immune disorders, including such disorders as inflammatory diseases, autoimmune, chronic and infectious diseases, such as AIDS, cancer, hypercholestemia, insulin disorders such as diabetes, growth disorders, various blood disorders including various anemias, thalassemias and hemophilia; genetic defects such as cystic fibrosis, Gaucher's Disease, Hurler's Disease, adenosine deaminase (ADA) deficiency, emphysema, or the like.

To exemplify the invention, the gene encoding erythropoietin (EPO) can be used. EPO is a glycoprotein hormone produced in fetal liver and adult kidney which acts on progenitor cells in the bone marrow and other hematopoietic tissue to stimulate the formation of red blood cells. Genes encoding human and other mammalian EPO have been cloned, sequenced and expressed, and show a high degree of sequence homology in the coding region across species. Wen et al. (1993) *Blood* 82:1507–1516. The sequence of the gene encoding native human EPO, as well as methods of obtaining the same, are described in, e.g., U.S. Pat. Nos. 4,954,437 and 4,703,008, incorporated herein by reference in their entirety, as well as in Jacobs et al. (1985) *Nature* 313:806–810; Lin et al. (1985) *Proc. Natl. Acad. Sci. USA* 82:7580; International Publication Number WO 85/02610; and European Patent Publication Number 232,034 B1. In addition, the sequences of the genes encoding native feline, canine and porcine EPO are known and readily available (GenBank Accession Nos.: L10606; L13027; and L10607, respectively), and the sequence of the gene encoding monkey (*Macaca mulatta*) is also known and available (GenBank Accession No.: L10609). The term "EPO" as used herein refers to the native, full-length secreted form of EPO, as well as to analogs or derivatives thereof comprising single or multiple amino acid substitutions, deletions or additions which retain EPO function or activity. In this regard, a number of small peptides have been identified which bind to and activate the receptor for EPO. Wrighton et al. (1996) *Science* 273:458–463; Livnah et al. (1996) *Science* 273:464–471. The recombinant AAV virions described herein which include a gene encoding EPO, or encoding an analog or derivative thereof having the same function, are particularly useful in the treatment of blood disorders characterized by defective red blood cell formation, such as in the treatment of anemia. Increased red blood cell production due to the production of EPO can be readily determined by an appropriate indicator, such as by comparing hematocrit measurements pre- and post-treatment, measuring increases in red blood cell count, hemoglobin concentration, or in reticulocyte counts. As described above, the EPO gene is flanked by AAV ITRs.

Alternatively, a nucleotide sequence encoding the lysosomal enzyme acid α-glucosidase (GAA) can be used. GAA functions to cleave α-1,4 and α-1,6 linkages of lysosomal glycogen to release monosaccharides. The sequence of the gene encoding human GAA, as well as methods of obtaining the same, have been previously described (GenBank Accession Numbers: M34424 and Y00839; Martiniuk et al. (1990) *DNA Cell Biol.* 9:85–94; Martiniuk et al. (1986) *Proc. Natl. Acad. Sci. USA* 83:9641–9644; Hoefsloot et al. (1988) *Eur. Mol. Biol. Organ.* 7:1697–1704). Thus, the recombinant AAV virions described herein can include a nucleotide sequence encoding GAA, or encoding an analog or derivative thereof having GAA activity.

The selected nucleotide sequence, such as EPO or another gene of interest, is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter; mouse mammary tumor virus LTR promoter; adenovirus major late promoter (Ad MLP); herpes simplex virus (HSV) promoters; a cytomegalovirus (CMV) promoter such as the CMV immediate early promoter region (CMVIE); a rous sarcoma virus (RSV) promoter; synthetic promoters; hybrid promoters; and the like. In addition, sequences derived from nonviral genes, such as the murine metallothionein gene, will also find use herein. Such promoter sequences are commercially available from, e.g., Stratagene (San Diego, Calif.).

For purposes of the present invention, control elements, such as muscle-specific and inducible promoters, enhancers and the like, will be of particular use. Such control elements include, but are not limited to, those derived from the actin and myosin gene families, such as from the myoD gene family (Weintraub et al. (1991) *Science* 251:761–766); the myocyte-specific enhancer binding factor MEF-2 (Cserjesi and Olson (1991) *Mol. Cell Biol.* 11:4854–4862); control elements derived from the human skeletal actin gene (Muscat et al. (1987) *Mol. Cell Biol.* 7:4089–4099) and the cardiac actin gene; muscle creatine kinase sequence elements (Johnson et al. (1989) *Mol. Cell Biol.* 9:3393–3399) and the murine creatine kinase enhancer (mCK) element; control elements derived from the skeletal fast-twitch troponin C gene, the slow-twitch cardiac troponin C gene and the slow-twitch troponin I gene; hypoxia-inducible nuclear factors (Semenza et al. (1991) *Proc. Natl. Acad. Sci. USA* 88:5680–5684; Semenza et al. *J. Biol. Chem.* 269:23757–23763); steroid-inducible elements and promoters, such as the glucocorticoid response element (GRE) (Mader and White (1993) *Proc. Natl. Acad. Sci. USA* 90:5603–5607); the fusion consensus element for RU486 induction; elements that provide for tetracycline regulated gene expression (Dhawan et al. (1995) *Somat. Cell. Mol. Genet.* 21:233–240; Shockett et al. (1995) *Proc. Natl. Acad. Sci. USA* 92:6522–6526; and inducible, synthetic humanized promoters (Rivera et al. (1996) *Nature Med.* 2:1028–1032).

These and other regulatory elements can be tested for potential in vivo efficacy using the in vitro myoblast model, which mimics quiescent in vivo muscle physiology, described in the examples below.

The AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988) Molec. Cell. Biol. 8:3988–3996; Vincent et al. (1990) Vaccines 90 (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; Kotin, R. M. (1994) *Human Gene Therapy* 5:793–801; Shelling and Smith (1994) *Gene Therapy* 1:165–169; and Zhou et al. (1994) *J. Exp. Med.* 179:1867–1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM MgCl$_2$, 10 mM DTT, 33 µg/ml BSA, 10 mM–50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 30–100 µg/ml total DNA concentrations (5–100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of one or more selected nucleic acid sequences. Preferred codons for expression of the chimeric gene sequence in mammalian muscle cells can be used. The complete chimeric sequence is assembled from overlapping oligonucleotides prepared by standard methods. See, e.g., Edge, *Nature* (1981) 292:756; Nambair et al. *Science* (1984) 223:1299; Jay et al. *J. Biol. Chem.* (1984) 259:6311.

In order to produce rAAV virions, an AAV expression vector is introduced into a suitable producer cell using known techniques, such as by transfection. A number of transfection techniques are generally known in the art. See, e.g., Graham et al. (1973) *Virology,* 52:456, Sambrook et al. (1989) *Molecular Cloning, a laboratory manual,* Cold Spring Harbor Laboratories, New York, Davis et al. (1986) *Basic Methods in Molecular Biology,* Elsevier, and Chu et al. (1981) *Gene* 13:197. Particularly suitable transfection methods include calcium phosphate co-precipitation (Graham et al. (1973) *Virol.* 52:456–467), direct microinjection into cultured cells (Capecchi, M. R. (1980) *Cell* 22:479–488), electroporation (Shigekawa et al. (1988) *BioTechniques* 6:742–751), liposome mediated gene transfer (Mannino et al. (1988) *BioTechniques* 6:682–690), lipid-mediated transduction (Felgner et al. (1987) *Proc. Natl. Acad. Sci. USA* 84:7413–7417), and nucleic acid delivery using high-velocity microprojectiles (Klein et al. (1987) *Nature* 327:70–73).

For the purposes of the invention, suitable producer cells for producing rAAV virions include microorganisms, yeast cells, insect cells, and mammalian cells, that can be, or have been, used as recipients of a heterologous DNA molecule. The term includes the progeny of the original cell which has been transfected. Thus, a "producer cell" as used herein generally refers to a cell which has been transfected with an exogenous DNA sequence. Cells from the stable human cell line, 293 (readily available through, e.g., the American Type Culture Collection under Accession Number ATCC CRL1573) are preferred in the practice of the present invention. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

2. AAV Helper Functions

Producer cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) *Current Topics in Microbiol. and Immunol.* 158:97–129; and Kotin, R. M. (1994) *Human Gene Therapy* 5:793–801. Suitable homologues of the AAV rep coding region include the human herpesvirus 6 (HHV-6) rep gene which is also known to mediate AAV-2 DNA replication (Thomson et al. (1994) *Virology* 204:304–311)

By "AAV cap coding region" is meant the art-recognized region of the AAV genome which encodes the capsid proteins VP1, VP2, and VP3, or functional homologues thereof. These cap expression products are the capsid proteins which are collectively required for packaging the viral genome. For a description of the AAV cap coding region, see, e.g., Muzyczka, N. and Kotin, R. M. (supra).

AAV helper functions are introduced into the producer cell by transfecting the cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822–3828; and McCarty et al. (1991) *J. Virol.* 65:2936–2945. A number of other vectors have been described which encode Rep and/or Cap expression products. See, e.g., U.S. Pat. No. 5,139,941.

Both AAV expression vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the invention include the hygromycin B resistance gene (encoding Aminoglycoside phosphotranferase (APH)) that allows selection in mammalian cells by conferring resistance to G418 (available from Sigma, St. Louis, Mo.). Other suitable markers are known to those of skill in the art.

3. Accessory Functions

The producer cell must also be rendered capable of providing non AAV derived functions, or "accessory functions," in order to produce rAAV virions. Accessory functions are non AAV derived viral and/or cellular functions upon which AAV is dependent for its replication. Thus, accessory functions include at least those non AAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

Particularly, accessory functions can be introduced into and then expressed in producer cells using methods known to those of skill in the art. Commonly, accessory functions are provided by infection of the producer cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) *J. Virol.* 40:241–247; McPherson et al. (1985) *Virology* 147:217–222; Schlehofer et al. (1986) *Virology* 152:110–117.

Alternatively, accessory functions can be provided using an accessory function vector. Accessory function vectors include nucleotide sequences that provide one or more accessory functions. An accessory function vector is capable of being introduced into a suitable producer cell in order to support efficient AAV virion production in the cell. Accessory function vectors can be in the form of a plasmid, phage, transposon or cosmid. Accessory vectors can also be in the form of one or more linearized DNA or RNA fragments which, when associated with the appropriate control elements and enzymes, can be transcribed or expressed in a producer cell to provide accessory functions.

Nucleic acid sequences providing the accessory functions can be obtained from natural sources, such as from the genome of an adenovirus particle, or constructed using recombinant or synthetic methods known in the art. In this regard, adenovirus-derived accessory functions have been widely studied, and a number of adenovirus genes involved in accessory functions have been identified and partially characterized. See, e.g., Carter, B. J. (1990) "Adeno-Associated Virus Helper Functions," in *CRC Handbook of Parvoviruses*, vol. I (P. Tijssen, ed.), and Muzyczka, N. (1992) *Curr. Topics. Microbiol. and Immun.* 158:97–129. Specifically, early adenoviral gene regions E1a, E2a, E4, VAI RNA and, possibly, E1b are thought to participate in the accessory process. Janik et al. (1981) *Proc. Natl. Acad. Sci. USA* 78:1925–1929. Herpesvirus-derived accessory functions have been described. See, e.g., Young et al. (1979) *Prog. Med. Virol.* 25:113. Vaccinia virus-derived accessory functions have also been described. See, e.g., Carter, B. J. (1990), supra., Schlehofer et al. (1986) *Virology* 152:110–117.

As a consequence of the infection of the producer cell with a helper virus, or transfection of the producer cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the producer cell using a variety of conventional purification methods, such as CsCl gradients. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions are then ready for use for DNA delivery, such as in gene therapy applications, for the production of transgenic animals, in vaccination, and particularly for the delivery of genes to a variety of muscle cell types.

4. In vitro and In vivo Delivery of rAAV Virions

Generally, rAAV virions are introduced into a muscle cell using either in vivo or in vitro transduction techniques. If transduced in vitro, the desired recipient muscle cell will be removed from the subject, transduced with rAAV virions and reintroduced into the subject. Alternatively, syngeneic or xenogeneic muscle cells can be used where those cells will not generate an inappropriate immune response in the subject.

Suitable methods for the delivery and introduction of transduced cells into a subject have been described. For example, cells can be transduced in vitro by combining recombinant AAV virions with muscle cells e.g., in appropriate media, and screening for those cells harboring the DNA of interest using conventional techniques such as Southern blots and/or PCR, or by using selectable markers. Transduced cells can then be formulated into pharmaceutical compositions, described more fully below, and the composition introduced into the subject by various techniques, such as by intramuscular, intravenous, subcutaneous and intraperitoneal injection, or by injection into smooth and cardiac muscle, using e.g., a catheter.

For in vivo delivery, the rAAV virions will be formulated into pharmaceutical compositions and will generally be administered parenterally, e.g., by intramuscular injection directly into skeletal or cardiac muscle.

Pharmaceutical compositions will comprise sufficient genetic material to produce a therapeutically effective amount of the protein of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

Appropriate doses will depend on the mammal being treated (e.g., human or nonhuman primate or other mammal), age and general condition of the subject to be treated, the severity of the condition being treated, the particular therapeutic protein in question, its mode of administration, among other factors. An appropriate effective amount can be readily determined by one of skill in the art.

Thus, a "therapeutically effective amount" will fall in a relatively broad range that can be determined through clinical trials. For example, for in vivo injection, i.e., injection directly to skeletal or cardiac muscle, a therapeutically effective dose will be on the order of from about $10^6$ to $10^{15}$ of the rAAV virions, more preferably $10^8$ to $10^{14}$ rAAV virions. For in vitro transduction, an effective amount of rAAV virions to be delivered to muscle cells will be on the order of $10^8$ to $10^{13}$ of the rAAV virions. The amount of transduced cells in the pharmaceutical compositions will be from about $10^4$ to $10^{10}$ muscle cells, more preferably $10^5$ to $10^8$ muscle cells. When the transduced cells are introduced to vascular smooth muscle, a lower dose may be appropriate. Other effective dosages can be readily established by one of ordinary skill in the art through routine trials establishing dose response curves.

Dosage treatment may be a single dose schedule or a multiple dose schedule. Moreover, the subject may be administered as many doses as appropriate. One of skill in the art can readily determine an appropriate number of doses.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Vector constructs

A. Construction of p1909adhlacZ.

Plasmid p1909adhlacZ was used as the helper construct in the following examples and was constructed from plasmid pWadhlacZ. Plasmid pWadhlacZ was constructed by partially digesting plasmid pUC119 (GeneBank Reference Name: U07649, GeneBank Accession Number: U07649) with AflIII and BspHI, blunt-end modifying with the klenow enzyme, and then ligating to go form a circular 1732 bp plasmid containing the bacterial origin and the amp gene only (the polylinker and F1 origin was removed). The blunted and ligated AflIII and BspHI junction forms a unique NspI site. The 1732 bp plasmid was cut with NspI, blunt-end modified with T4 polymerase, and a 20 bp HinDIII-HinCII fragment (blunt-end modified with the klenow enzyme) obtained from the pUC119 polylinker was ligated into the blunted NspI site of the plasmid. The HinDIII site from the blunted polylinker was regenerated, and then positioned adjacent to the bacterial origin of replication. The resulting plasmid was then cut at the unique PstI/Sse8387I site, and an Sse8387I-PvuII-Sse8387I oligonucleotide, having the sequence: 5'-GGCAGCTGCCTGCA-3' (SEQ ID NO.:1), was ligated therein. The remaining unique BspHI site was cut, blunt-end modified with klenow enzyme, and an AscI linker oligonucleotide, having the sequence: 5'-GAAGGCGCGCCTTC-3' (SEQ ID NO.:2) was ligated therein, eliminating the BspHI site. The resulting plasmid was called pWee.

In order to create the pWadhlacZ construct, a CMVlacZ expression cassette (comprising a nucleotide sequence flanked 5' and 3' by AAV ITRs, containing the following elements: a CMV promoter, the hGH 1st intron, an adhlacz fragment and an SV40 early polyadenylation site) was inserted into the unique PvuII site of pWee using multiple steps such that the CMV promoter was arranged proximal to the bacterial amp gene of pWee.

More particularly, a CMVlacZ expression cassette was derived from the plasmid psub201CMV, which was constructed as follows. An oligonucleotide encoding the restriction enzyme sites:

NotI-MluI-SnaBI-AgeI-BstBI-BssHII-NcoI-HpaI-BspEI-PmlI-RsrII-NotI and having the following nucleotide sequence:
5'-GCGGCCGCACGCGTACGTACCGGTTCGAAGC GCGCACGGCCGACCATGGTTAAC TCCGGACACGTGCGGACCGCGGCCGC-3' (SEQ ID No.:3) was synthesized and cloned into the blunt-end modified KasI-EarI site (partial) of pUC119 to provide a 2757 bp vector fragment. A 653 bp SpeI-SacII fragment containing a nucleotide sequence encoding a CMV immediate early promoter was cloned into the SnaBI site of the 2757 bp vector fragment. Further, a 269 bp PCR-produced BstBI—BstBI fragment containing a nucleotide sequence encoding the hGH 1st intron which was derived using the following primers:

5'-AAAATTCGAACCTGGGGAGAAACCAGAG-3' (SEQ ID NO.:4) and

3'-aaaattcgaacaggtaagcgcccctTTG-5' (SEQ ID NO.:5), was cloned into the BstBI site of the 2757 bp vector fragment, and a 135 bp HpaI-BamHI (blunt-end modified) fragment containing the SV40 early polyadenylation site from the pCMV-β plasmid (CLONETECH) was cloned into the HpaI site of the subject vector fragment. The resulting construct was then cut with NotI to provide a first CMV expression cassette.

Plasmid pW1909adhlacZ was constructed as follows. A 4723 bp SpeI-EcoRV fragment containing the AAV rep and cap encoding region was obtained from the plasmid pGN1909 (ATCC Accession Number 69871). The pGN1909 plasmid is a high efficiency AAV helper plasmid having AAV rep and cap genes with an AAV p5 promoter region that is arranged in the construct to be downstream from its normal position (in the wild type AAV genome) relative to the rep coding region. The 4723 bp fragment was blunt-end modified, and AscI linkers were ligated to the blunted ends. The resultant fragment was then ligated into the unique AscI site of pWadhlacZ and oriented such that the AAV coding sequences were arranged proximal to the bacterial origin of replication in the construct.

Plasmid pW1909adhlacZ includes the bacterial beta-galactosidase (β-gal) gene under the transcriptional control of the cytomegalovirus immediate early promoter (CMVIE).

B. Construction of pW1909EPO.

Plasmid pW1909adhlacZ was modified to express human erythropoietin (EPO) by replacing the adhlacz gene with a 718 base pair PpuMI-NcoI fragment of human EPO cDNA (Wen et al. (1993) *Blood* 5:1507–1516) and by cloning a 2181 bp ClaI-EcoRI lacZ spacer fragment (noncoding) into the PmlI site of the vector.

C. Construction of pAAV-GAA.

A plasmid containing the human lysosomal enzyme acid α-glucosidase (GAA) coding region was constructed as follows. A 3.2 kB cDNA clone containing the coding sequence for human GAA beginning 207 bps downstream from the initiation codon (GenBank Accession Numbers: M34424 and Y00839; Martiniuk et al. (1990) *DNA Cell Biol.* 9:85–94) was cloned into the EcoRI site of Bluescript KS (Stratagene). Additional 5' sequence was generated using polymerase chain reaction (PCR) with reverse-transcribed poly-A mRNA (obtained from normal human fibroblasts) as the template. The 5' primer was constructed with a KpnI restriction site and bps −3 to 12 of the published sequence (Martiniuk et al. (1986) *Proc. Natl. Acad. Sci. USA* 83:9641–9644; Hoefsloot et al. (1988) *Eur. Mol. Biol. Organ.* 7:1697–1704). The 3' primer was synthesized from basepairs 1001 to 1018. Using KpnI and the unique internal StuI site at position 776, the PCR product was ligated to the partial cDNA to form the full-length GAA-encoding plasmid. The full length cDNA was truncated at a unique SphI restriction site, and cloned into the expression vector p1.1c to result in the pAAV-GAA construct having the GAA coding region under transcriptional control of the CMV-IE promoter.

The p1.1c expression vector was constructed as follows. pUC119 was partially digested with KasI and EarI, and a 2713 bp vector fragment containing the ampicillin resistance gene, the coli 1 origin of replication and the M13 origin of replication, was isolated, blunt end modified, and ligated to a synthetic DNA polylinker encoding the restriction enzyme sites NotI-MluI-SnaBI-AgeI-SfuI-BssHII-EagI-NcoI-PmeI-BspEI-PmlI-RsrII-NotI, and having the following nucleotide sequence:

5'-GCGGCCGCACGCGTTGTTAACAACCGGTTCGA
AGCGCG CAGCGGCCGACCATGGGTT
TAAACTCCGGACCACGTGCGGACCG
AGCGGCCGC-3' (SEQ ID NO.:6). The ligation was conducted such that the MluI end of the polylinker was ligated to the KasI side of the plasmid. A 653 bp SpeI-SacII fragment encoding the CMV immediate-early promoter, a 269 bp PCR-produced SfuI-SfuI produced fragment encoding the hGH 1st intron (derived using the following primers: 5'-AAAATTCGAACAGGTAAGCGCCCCTTTG-3' (SEQ ID NO.:7) and 3'-AAAATTCGAACCTGGGGAGAAACCAGAG-5' (SEQ ID NO.:8)), a 183 bp BssHII-BssHII polylinker fragment from pBluescript II SK-, and a 135 bp HpaI-BamHI (blunted) fragment containing the SV40 early polyadenylation site from pCMV-β (Stratagene), were cloned into the SnaBI, SfuI, BssHII, and PmeI sites, respectively, of the aforementioned plasmid. The orientation of the polylinker relative to the intron and polyadenylation site was intron-polylinker (5'SacI-3'KpnI)-polyadenylation site. The polylinker was further modified by removing the 88 bp SacI-XhoI polylinker fragment and replacing it with the following synthetic SacI to XhoI fragment encoding the restriction enzyme sites SacI-ClaI-EcoRI-SmaI-BamHI-XbaI-SalI-PstI-BstXI-EcoRV-BstXI-olmeganuclease-HinDIII-XhoI, having the following nucleotide sequence:

5'-GAGCTCAATCGATTGAATTCCCCGGGGATCCT
CTAGAGTCGACCTGCAGCCACT GTGTTG-
GATATCCAACACACTGGTAGGGATAA
CAGGGTAATCTCGAG-3' (SEQ ID NO.:9).

Viruses and Cell Lines

Adenovirus type 2 (Ad2), available from the American Type Culture Collection, ATCC, Catalogue Number VR846, was used as helper virus to encapsidate vectors.

The human 293 cell line (Graham et al. (1977) *J. Gen. Virol.* 36:59–72, available from the ATCC under Accession no. CRL1573), which has adenovirus E1a and E1b genes stably integrated in its genome, was cultured in complete Dulbecco's modified Eagle's media (DMEM; Bio-Whittaker, Walkersville, Md.) containing 4.5 g/L glucose, 10% heat-inactivated fetal bovine serum (FBS; Hyclone, Logan, Utah), 2 mM glutamine, and 50 units/mL penicillin and 50 μg/mL streptomycin.

The C2C12 murine myoblast cell line, available from the ATCC, Catalogue Number CRL1772, was cultured in DMEM with 20% fetal calf serum (FCS), 1% chick embryo extract and 5 μg/mL gentamicin.

Fetal human skeletal myoblasts (Clonetics) were cultured in Hams F-12 human growth medium, containing 20% FCS and 5 μg/mL gentamicin.

The above cell lines were incubated at 37° C. in 5% $CO_2$, and were routinely tested and found free of mycoplasma contamination.

Production of Recombinant AAV Virions

Recombinant AAV virions were produced in human 293 cells as follows. Subconfluent 293 cells were cotransfected by standard calcium phosphate precipitation (Wigler et al. (1979) *Proc. Natl. Acad. Sci USA* 76:1373–1376) with one of the AAV vector/helper plasmid constructs, pW1909adhLacZ or pW1909EPO; or with PAAV-GAA and the pW1909 helper plasmid. After 6 hours, the transfected cells were infected with Ad2 in fresh medium at a multiplicity of infection (MOI) of 2, and incubated at 37° C. in 5% $CO_2$ for 70 hours prior to harvest. Pelleted cells were lysed in Tris buffer (10 mM Tris, 150 mM NaCl, pH 8.0) by three cycles of freeze-thaw. The lysate was clarified of cell debris by centrifugation at 12,000×g, and the crude-cell lysate was layered onto a cesium chloride cushion for isopyknic gradient centrifugation. Recombinant AAV virions (rAAV-LacZ, rAAV-hEPO, or rAAV-hGAA virions) were extracted from the resulting gradient by isolating the fractions with an average density of approximately 1.38 g/mL, resuspended in Hepes buffered saline (HBS) containing 50 mM Hepes (pH 7.4) and 150 mM NaCl. The preparations were then heated at 56° C. for approximately 1 hour to inactivate Ad2.

Assay of rAAV by Dot-blot Hybridization

Recombinant AAV virions were DNase I digested, proteinase K treated, phenol-chloroform extracted, and DNA precipitated with sodium acetate-glycogen (final concentrations=0.3 M sodium acetate and 160 μg/mL, respectively). DNA samples were denatured (200 μL of 2× alkaline solution (0.8 M NaOH, 20 mM EDTA) added to DNA sample) for 10 minutes, then added to appropriate wells in a dot-blot apparatus, and blotted onto wet Zeta Probe membrane (BioRad), by applying suction until wells were empty. Then, 400 μL of 1× alkaline solution was added; after 5 minutes, wells were emptied by suction. The membrane was rinsed in 2× SSC (Sambrook et al., supra) for 1 min, drained, air dried on filter paper, then baked in vacuum at 80° C. for 30 min. The membrane was then prehybridized for 30 min at 65° C. with 10 mL hybridization buffer (70 SDS, 0.25 M Sodium Phosphate, pH 7.2, 1 mM EDTA). Buffer was replaced with 10 mL fresh solution, freshly boiled probe added, and hybridized overnight at 65° C. The membrane was washed twice with 25 mL of wash-1 buffer (5% SDS, 40 mM sodium phosphate, pH 7.2, 1 mM EDTA) for 20 min at 65° C. and twice with wash-2 buffer (1% SDS, 40 mM sodium phosphate, pH 7.2, 1 mM EDTA). The membrane was wrapped in plastic film, exposed to radiographic film, and appropriate dots excised from the membrane to determine radioactivity by scintillation counting, and quantitated by comparison with standards. Titers of rAAV virion were routinely in the range of approximately $10^{13}$ genomes/mL.

Assay for Contaminating Helper Adenovirus

Contaminating infectious adenovirus was assayed as follows. Samples from the purified rAAV virion stocks were added to 50% confluent 293 cells (cultured in 12 well dishes at $1\times10^5$ cells/well), and the cultures were passaged for 30 days (e.g., the cultures were split 1 to 5, every 3 days) or until the culture exhibited 100% cytopathic effect (CPE) due to adenovirus infection. Cultures were examined daily for CPE, and the day upon which each experimental culture showed 100% CPE was noted. Reference 293 cell cultures infected with a range of known amounts of adenovirus type-2 (from 0 to $1\times10^7$ plaque forming units (pfu)/culture) were also prepared and treated in the same manner. A standard curve was then prepared from the data obtained from the reference cultures, where the adenovirus pfu number was plotted against the day of 100% CPE. The titer of infectious adenovirus type-2 in each experimental culture was then readily obtained as determined from the standard curve. The limit of detection of the assay was 100 pfu/mL. The presence of wild-type AAV contamination, analyzed by dot-blot hybridization, was approximately 7 logs lower than recombinant virion concentration.

Differentiation of Myoblasts

C2C12 myoblasts were transduced either while actively dividing, or as a differentiated cell culture. Differentiation was induced by placing subconfluent myoblasts in murine differentiation medium (DMEM containing 2% horse serum and standard concentrations of glutamine and penicillin-streptomycin) for an interval of four days prior to transduction in order to induce myoblast fusion and formation of differentiated myotubes.

Fetal human skeletal myoblasts were differentiated in human differentiation medium (DMEM containing 10% horse serum and 5 μg/mL gentamicin). Verification of differentiation was performed by microscopic analysis to determine the presence of multinucleated myotubes in culture.

EXAMPLE 1

Expression of rAAV-LacZ in Terminally Differentiated Adult Rat Cardiomyocytes

The ability of recombinant AAV virions to transduce terminally differentiated adult cardiomyocytes was established in vitro. Cardiomyocytes were harvested by coronary perfusion with collagenase of adult rat hearts (Fischer 344, Harlan Sprague Dawley, Indianapolis, Ind.). Cardiomyocytes were grown on laminin-coated glass coverslips and exposed to rAAV-LacZ virions for 4 hours. After 72 hours, the cells were stained for β-galactosidase activity. AAV expression was detected by blue staining of the binucleated cells. These studies demonstrated the ability of rAAV virions to transduce terminally differentiated cells. The transduction efficiency in vitro was 30% of adult cells at a multiplicity of infection (MOI) of $10^4$ genomes per cell.

EXAMPLE 2

Stability of rAAV-LacZ Expression In Vivo

Adult Fischer rats were used to analyze expression of transgenes in vivo. Incremental doses of rAAV-LacZ virions were injected into the left ventricular apex of the heart using either a subxyphoid or lateral thoracotomy approach. More particularly, experimental animals were anesthetized with Metofane followed by a subxyphoid incision to expose the diaphragmatic surface of the heart. Apical cardiac injections were performed with a glass micropipette. Recombinant virion was diluted in normal saline and injected at a volume of 20–50/μL.

At varying times post-injection, hearts were harvested and examined for β-galactosidase production and for the presence of infiltrating mononuclear cells. For 5-Bromo-4-chloro-3-indolyl β-D-galactoside histochemical determination, frozen sections (6 μm) were fixed in 0.5% glutaraldehyde and stained for β-galactosidase activity as described (Sanes et al. (1986) "Use of Recombinant Retrovirus to Study Post-Implantation Cell Lineage in Mouse Embryos," *EMBO J* 5:3133–3142). Paraffin sections (5 μm) were stained with hematoxylin/eosin. Sections were examined for infiltrating mononuclear cells.

The above-described histochemical studies showed greater than 50% transduction of cardiomyocytes in the region of injection at each time point examined. Further, there was no inflammatory cell infiltrate noted during the course of analysis. β-galactosidase staining was observed to persist in cardiac muscle for at least two months following gene transfer.

EXAMPLE 3

In vivo Transduction of Murine Skeletal Muscle using rAAV-LacZ Virions

Recombinant AAV-LacZ virions were injected into muscle tissue of mice, and transduction assessed by β-gal activity. Particularly, in vivo transduction was performed by intramuscular (IM) injection of recombinant AAV virions into the skeletal muscle of healthy 6–8 week old Balb/c mice (Jackson Laboratories, Bar Harbor, Me., Simonsen Laboratories, Gilroy, Calif., or Harlan Laboratories) under either Metofane (Pitman-Moore, Mundelein, Ill.) or ketamine-xylazine anesthesia. The mid-portion of each tibialis anterior muscle was exposed via a 1 cm incision. Injections into the tibialis anterior were carried out using a micro-capillary tube attached to a Hamilton syringe to administer the following formulations at a depth of 2 mm: phosphate-buffered saline (PBS) alone (negative control); or PBS containing either rAAV-LACZ virions or pW1909adhlacZ plasmids.

Tissue samples of tibialis anterior muscle, forelimb muscle, heart, brain and liver were obtained for analysis of β-galactosidase expression. One tibialis anterior muscle from each animal was processed for cross-sectional β-galactosidase analysis, and total β-galactosidase was determined from a crude homogenate of the other muscle using a chemiluminescent assay.

For histochemical detection of β-galactosidase, muscle samples were snap-frozen in dry ice-cooled isopentane, followed by serial transverse sectioning (10 μm) and processing according to previously described methods (Sanes et al. (1986) *EMBO J* 5:3133–3142). The cross-sectional area of the tibialis anterior expressing β-galactosidase was determined as follows: after counter-staining with nuclear fast red (Vector Labs), the X-gal stained tissue was digitally photographed and the cross-sectional area of stored images was determined using NIH Image software.

The GALACTO-LIGHT™ (Tropix, Bedford, Mass.) chemiluminescent reporter assay kit was used to detect total β-galactosidase activity in the entire tibialis anterior muscle. Standard curves were prepared from known amounts of purified β-galactosidase (Sigma, St. Louis, Mo.) resuspended in non-transduced muscle homogenate. β-galactosidase activity is expressed as either: nanograms of β-galactosidase, normalized for the entire muscle, minus background activity; or in terms of relative light units (RLU) as quantified by luminometer. Forelimb muscle, cardiac muscle, brain tissue and liver samples were assayed in an identical fashion.

A. Time course of β-galactosidase expression.

A single intramuscular injection into the left and right tibialis anterior muscles (under direct vision) was used to deliver 8×10$^9$ rAAV-LacZ in a PBS vehicle. Four animals were injected with PBS alone. Animals were sacrificed at 2, 4, 8, 12, 24 and 32 weeks after injection, and the tibialis anterior muscle was excised and analyzed for the presence of bacterial β-galactosidase (n=5 for each group) as described above.

Efficiency of the LacZ gene transfer was assessed by cross-sectional tissue staining and chemiluminescent assay. As can be seen in FIG. 1 and in Table I below, gene expression persisted for at least 32 weeks. In addition, two weeks after injection of the recombinant virions, 18% of the muscle cross-sectional area expressed β-galactosidase, while at 32 weeks, 24% of the muscle cross-sectional area expressed β-galactosidase. Negative control tibialis anterior muscle (obtained from the animals injected with PBS alone) showed no background staining. Muscle β-galactosidase activity was also determined in the contralateral injected muscle. This study also revealed persistent expression for at least 32 weeks, in agreement with the cross-sectional fiber analysis (Table I). Further, the observed β-galactosidase was sustained with minimal inflammatory cell infiltrate. These data demonstrate that rAAV-LacZ virion administration into muscle results in stable expression of the transgene for at least 8 months.

Figure 2:
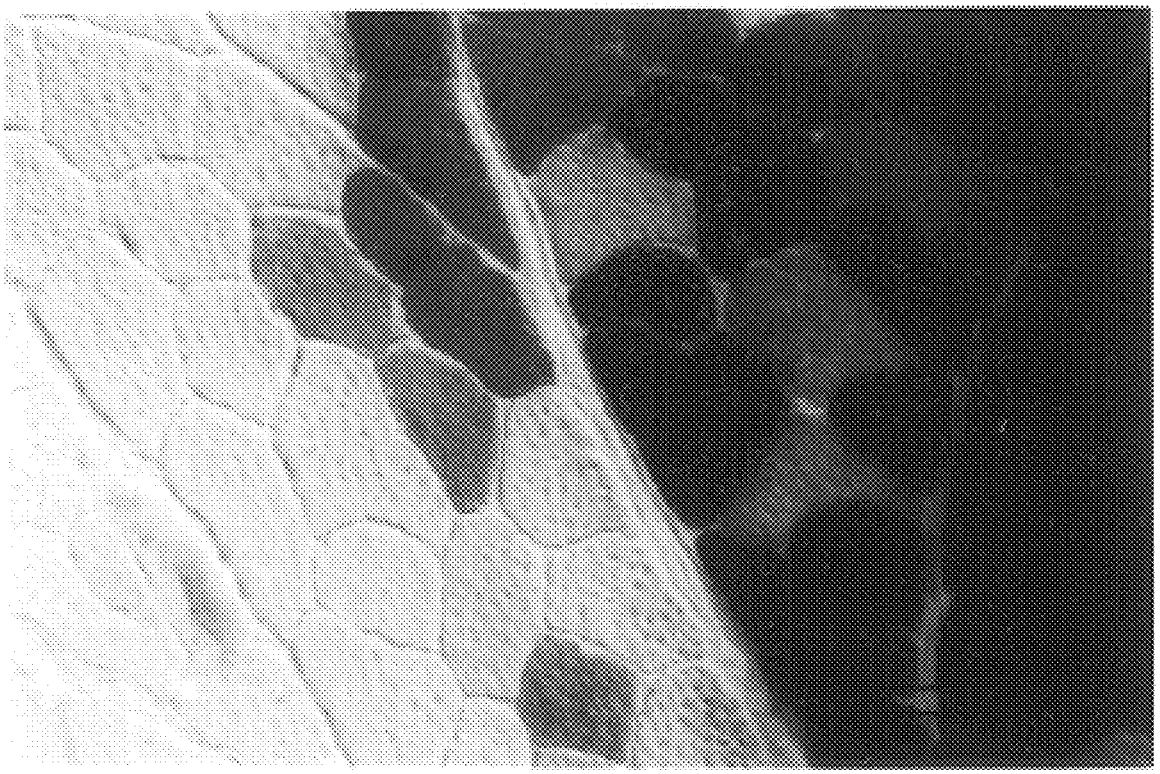
FIG. 2 shows a section of skeletal muscle two months after injection with rAAV-LacZ as described in Example 3, Part A. The tibialis anterior muscle was processed for in situ detection of β-galactosidase expression, and photographed with diffraction-interference contrast optics at 400×.

Upon histological examination, positive staining filled the cytoplasm of the transduced myofibers and was observed through large contiguous portions of the muscle. Serial transverse sections revealed that blue staining extended throughout the length of the muscle fiber. Diffraction-interference contrast microscopy revealed a clear delineation between positively and negatively stained myofibers (FIG. 2), suggesting that recombinant virion delivery was limited by structural barriers such as epimyseal or perimyseal connective tissue. Homogenates prepared from brain, heart, liver, and forelimb muscle displayed no β-galactosidase activity when compared with the background activity of the negative control animals.

TABLE 1

Time Course of β-galactosidase Expression
Following Single Injection with rAAV-LacZ

| Time (weeks) | β-galactosidase expression (ng/muscle) | Percent cross-sectional area expressing β-galactosidase (%) |
|---|---|---|
| 2 | 1441 ± 458 | 18 ± 6 |
| 4 | 951 ± 176 | 20 ± 4 |
| 8 | 839 ± 436 | 24 ± 3 |
| 12 | 1878 ± 521 | 29 ± 5 |
| 24 | 2579 ± 1165 | 22 ± 3 |
| 32 | 1242 ± 484 | 24 ± 3 |

The left and right tibialis anterior muscles were injected with 8×10$^9$ rAAV-lacZ. One member of the pair of injected muscles was processed for β-galactosidase expression (n=5±SEM). The other muscle was processed for histochemical detection of β-galactosidase and determination of the cross-sectional area of the tibialis anterior expressing β-galactosidase. Mean cross-sectional areas±SEM are shown.

B. Dose-response assay.

Figure 3:
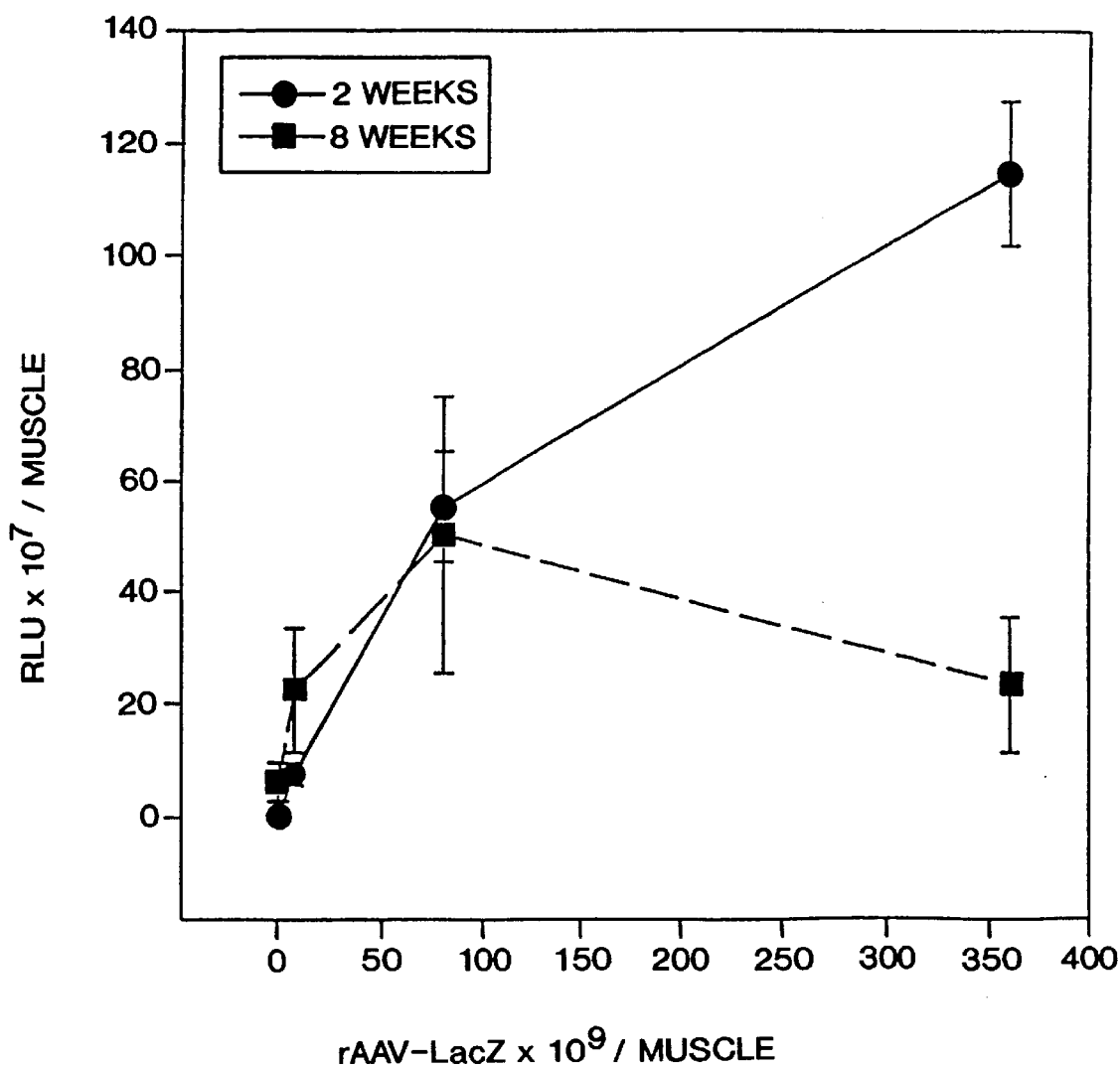
FIG. 3 depicts β-galactosidase expression in Balb/c mice tibialis anterior muscle transduced in vivo with rAAV-LacZ as described in Example 3, Part B. Adult Balb/c mice were injected intramuscularly (IM) with various doses of rAAV-LacZ. At 2 and 8 weeks post injection, tissue was harvested for analysis of beta-galactosidase (β-gal). β-gal expression was analyzed by measurement of relative light units (RLU) emitted from muscle homogenates, as detected by luminometer.

To determine the effective dose range for rAAV-LacZ in vivo, recombinant virions were injected into the tibialis anterior muscle of 6–8 week old Balb/c mice, and transduction assessed by β-galactosidase activity as measured by GLACTO-LIGHT™ relative light units (RLU). As can be seen in FIG. 3, at two weeks post-injection, the observed RLU ranged from approximately 0.2×10$^7$ RLU/muscle (injected with 8×10$^8$ rAAV-LacZ) to approximately 1.1×10$^9$ RLU/muscle (injected with 3.6×10$^{11}$ rAAV-LacZ).

The levels of expression of β-galactosidase measured in RLU correspond to the percentage of β-galactosidase-positive muscle fibers on cross-sectional analysis. For example, 0.2×10$^7$ RLU corresponds to approximately 1% β-galactosidase positive muscle fibers and 1.1×10$^9$ RLU corresponds to approximately 60% β-galactosidase positive muscle fibers.

C. Comparison of β-galactosidase expression efficiency.

A comparison of β-galactosidase expression efficiency obtained by in vivo transduction of mice using either rAAV-LacZ virions, or plasmid DNA containing the same LacZ expression cassette (pW1909adhlacZ) was carried out as follows. Either 8×10$^9$ rAAV-LacZ, or 100 μg of pW1909adhlacZ, was injected into the tibialis anterior muscle of 6–8 week old Balb/c mice. Two weeks post-injection, β-galactosidase activity was assessed using the GALACTO-LIGHT™ chemiluminescent reporter assay kit, as described above. Administration of the recombinant virions resulted in 1441 ng β-galactosidase/muscle (n=5), while administration of 100 μg of the plasmid DNA, a typical in vivo plasmid DNA dosage (Whalen et al. (1995) *Hum. Gene Ther.* 4:151–159), resulted in 12 ng β-galactosidase/muscle (n=4). This dosage of pW1909adhlacZ plasmid DNA is equivalent to 2.2×10$^{13}$ single stranded genomes, demonstrating that gene delivery by the recombinant virions was substantially more efficient than delivery of an equal molar quantity of vector DNA.

EXAMPLE 4

In vitro Transduction of Murine Myotubes and Myoblasts

In order to determine if differentiated cultured muscle cells are appropriate targets for recombinant AAV virion transduction, and to assess the ability of such cells to express a transduced gene, the following study was carried out. Murine C2C12 cells were selected since these cells have been extensively studied as a model for mammalian myogenesis (Blau et al. (1993) *Trends Genet.* 9:269–274), and can be induced to differentiate by growth in reduced serum medium.

In the study, C2C12 myoblasts (dividing cells) were seeded in cell culture plates at a density of 2×10$^4$ cells/cm$^2$, maintained in growth media (GM) until confluent, split, and then either cultured in GM or cultured for 5 days in murine DM. Differentiation was verified by the microscopic presence of multinucleate myotubes, representing fused myoblasts (differentiated C2C12 cells).

The C2C12 myotubes and myoblasts were transduced in culture with purified rAAV-hEPO virions at a MOI of 10$^5$ in OptiMEM (Gibco BRL). In the myotube cultures, DM was added after virion adsorption. The culture media of the transduced cells was changed 24 hours prior to collection of supernatants at 3, 8 and 14 days following transduction. Secretion of hEPO was assessed by ELISA using the human erythropoietin Quantikine IVD kit (available from R and D Systems, Minneapolis, Minn.) according to manufacturer's recommendations.

Figure 4:
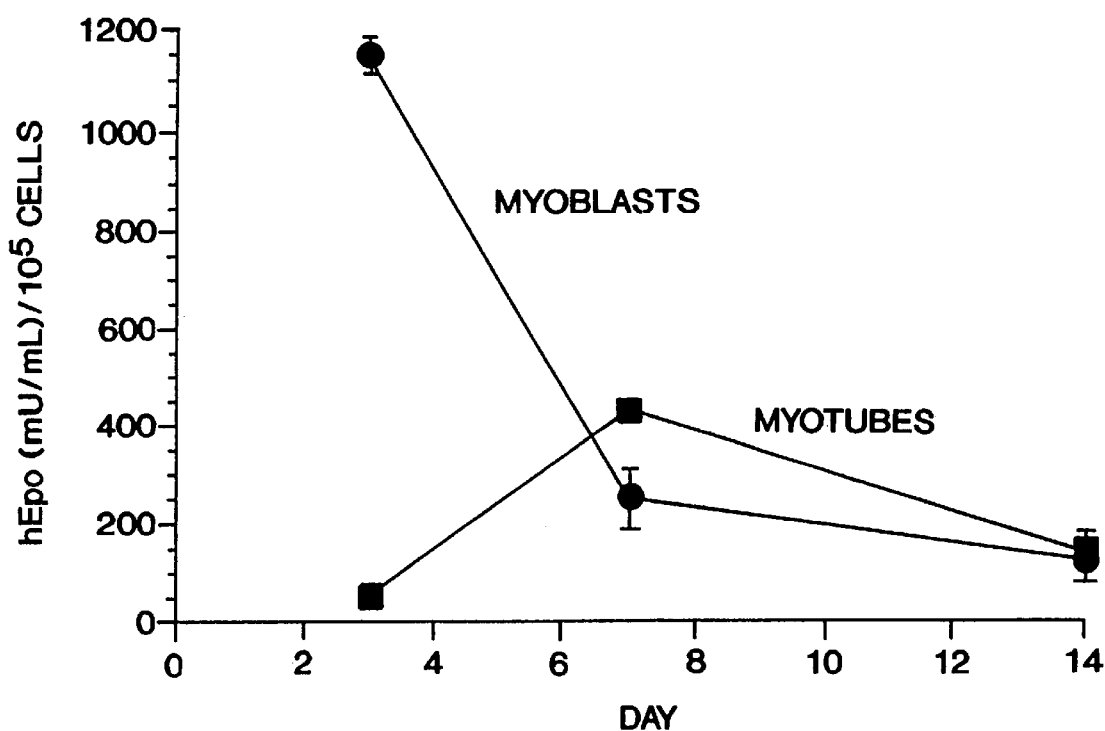
FIG. 4 shows the secretion of human erythropoietin (hEPO) from transduced myotubes and myoblasts, as described in Example 4. Myotubes (differentiated cells) or myoblasts (actively dividing cells) were transduced with rAAV-hEPO at a ratio of approximately $10^5$ per target cell. Levels of secreted hEPO were analyzed in supernatants at various time points. Baseline levels of hEPO prior to transduction were below the level of detection in both cell populations; the values at each time point represent replicate values +/− standard deviation.
Figure 5:
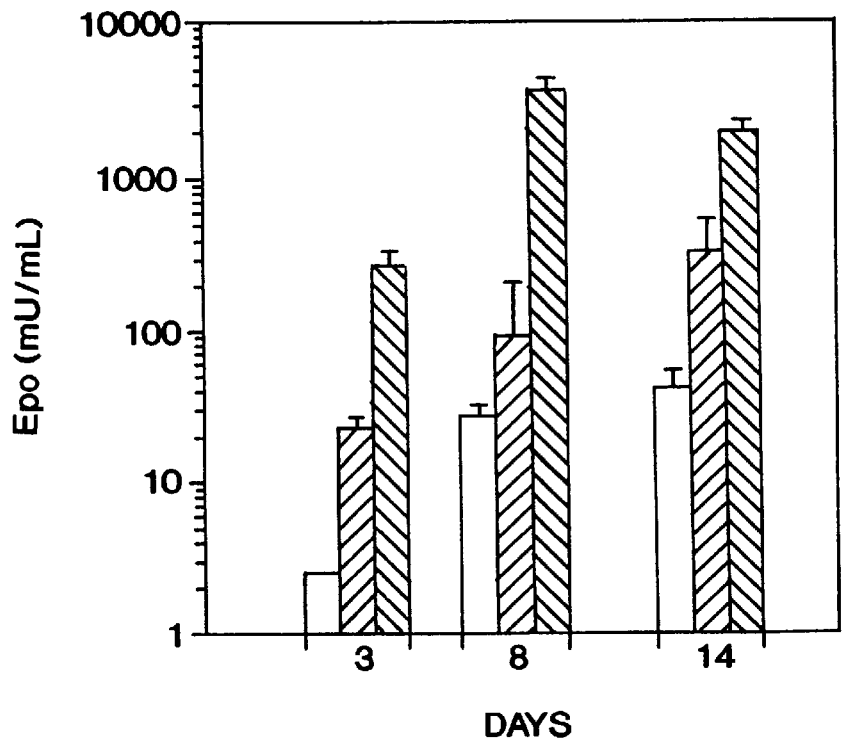
FIG. 5 shows the secretion of human erythropoietin (hEPO) by C2C12 myotubes transduced with rAAV-hEPO as described in Example 4. Confluent C2C12 myoblasts were differentiated into myotubes and transduced with $3 \times 10^8$ (open bar), $3 \times 10^9$ (left cross-hatched bar), or $3 \times 10^{10}$ (right cross-hatched bar) rAAV-hEPO. Secretion of EPO was measured 3, 8, and 14 days after transduction. Control rAAV-LacZ myotubes secreted <2.5 mU/mL EPO. The bar graph depicts mean production of EPO/well/24 hour as determined in triplicate cultures±the standard error of mean (SEM).

The results of the study show that hEPO is secreted from both the transduced myotubes and myoblasts. The levels of hEPO secretion increased in the myotubes over the first seven days post-transduction (FIG. 4). As can be seen by reference to FIG. 5, a dose-dependent increase in the secretion of hEPO was also observed in the transduced C2C12 myotubes. Eight days post-transduction of the myotubes, hEPO levels peaked at >3400 mU/mL. These data demonstrate that transduction with rAAV-hEPO of both myotubes or myoblasts results in hEPO secretion by the transduced cells, and that in short-term myotube cultures, hEPO is synthesized and secreted in a dose-dependent manner.

EXAMPLE 5

In vitro Transduction of Human Myotubes Using rAAV-hEPO Virions

To determine if differentiated primary human muscle cells are able to express hEPO following transduction with rAAV-hEPO, the following study was carried out. Primary fetal human skeletal myoblasts were seeded in cell culture plates at a density of $2 \times 10^4$ cells/cm$^2$, grown to confluence in appropriate growth media, and then cultured for 14 days in human DM. Differentiation was verified by microscopic examination for multinucleate cells. In vitro transduction was carried out by adding purified rAAV-hEPO virions to the cultured myotubes in OptiMEM medium (Gibco BRL). DM was added to the cultures after virion adsorption. Control cultures were transduced with rAAV-LacZ.

Culture media was changed 24 hours prior to collection of supernatants at day 3, 8 and 14 post transduction. Secreted EPO levels were assayed by ELISA as described above in Example 4.

Figure 6:
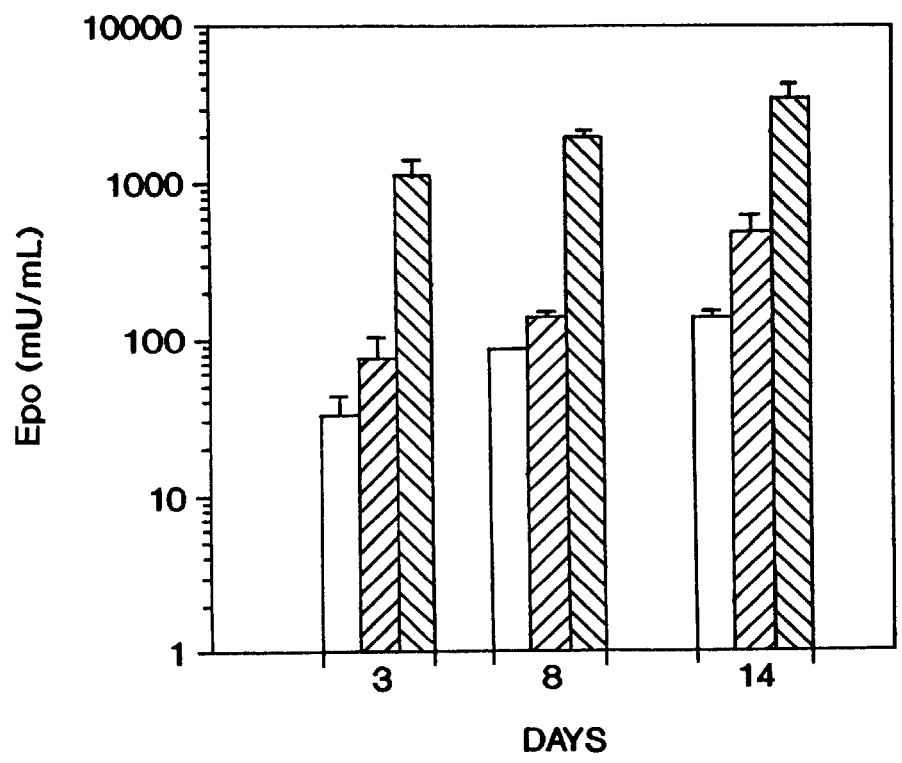
FIG. 6 shows the secretion of human erythropoietin (hEPO) by primary human myotubes transduced with rAAV-hEPO as described in Example 5. Confluent human myoblasts were differentiated into myotubes by culture for 14 days in reduced-serum media, then transduced with $3 \times 10^8$ (open bar), $3 \times 10^9$ (left cross-hatched bar), or $3 \times 10^{10}$ (right cross-hatched bar) rAAV-hEPO. Secretion of EPO was measured 3, 8 and 14 days after transduction. Control myotubes transduced with rAAV-LacZ secreted <2.5 mU/mL EPO. The bar graph depicts mean production of EPO/well/24 hour as determined in triplicate cultures±SEM.

As can be seen in FIG. 6, the transduced human myotubes secreted hEPO into the culture in a dose-dependent manner. No detectable EPO activity was measured in the control cultures. Secretion of EPO increased over the 14-day interval post-transduction. These data demonstrate that primary human myotubes transduced by recombinant AAV virions are capable of expressing and secreting erythropoietin.

EXAMPLE 6

Systemic Delivery of Human Erythropoietin In vivo by Intramuscular Administration of rAAV-hEPO Recombinant AAV virions encoding hEPO were administered to adult healthy Balb/c mice in vivo to determine if a systemic level of hEPO can be produced, and a biological response obtained. At various time points after administration, blood was obtained from the orbital venous plexus under anesthesia. Serum hEPO levels were determined by ELISA as described above. Red cell counts were done by hemocytometer, hematocrit was determined by centrifugation of blood in micro-capillary tubes, and hemoglobin concentration was analyzed by cyanmethemoglobin assay (DMA, Arlington, Tex.) according to manufacturer's specifications and compared with a standard (Stanbio Laboratory, San Antonio, Tex.) analyzed at 570 nm on a spectrophotometer. Reticulocytes were analyzed by either new methylene blue stain, or by FACS analysis of thiazole orange stained peripheral blood samples (RETIC-COUNT®, Becton-Dickinson, Mountain View, Calif.); the results of data obtained by either of these methods were similar.

An initial experiment revealed that high levels of hEPO and elevated hematocrits were maintained for >100 days in mice injected IM with $6.5 \times 10^{11}$ rAAV-hEPO. Next, adult female Balb/c mice were injected IM in both hind limbs with a single administration of rAAV-hEPO at dosages ranging from $3 \times 10^9$ to $3 \times 10^{11}$ particles. Control animals were injected with rAAV-LacZ. The resulting serum hEPO levels were analyzed and are reported below in Table II. As can be seen, a well-defined dose-response was obtained 20, 41, 62 and 83 days post injection.

Figure 7:
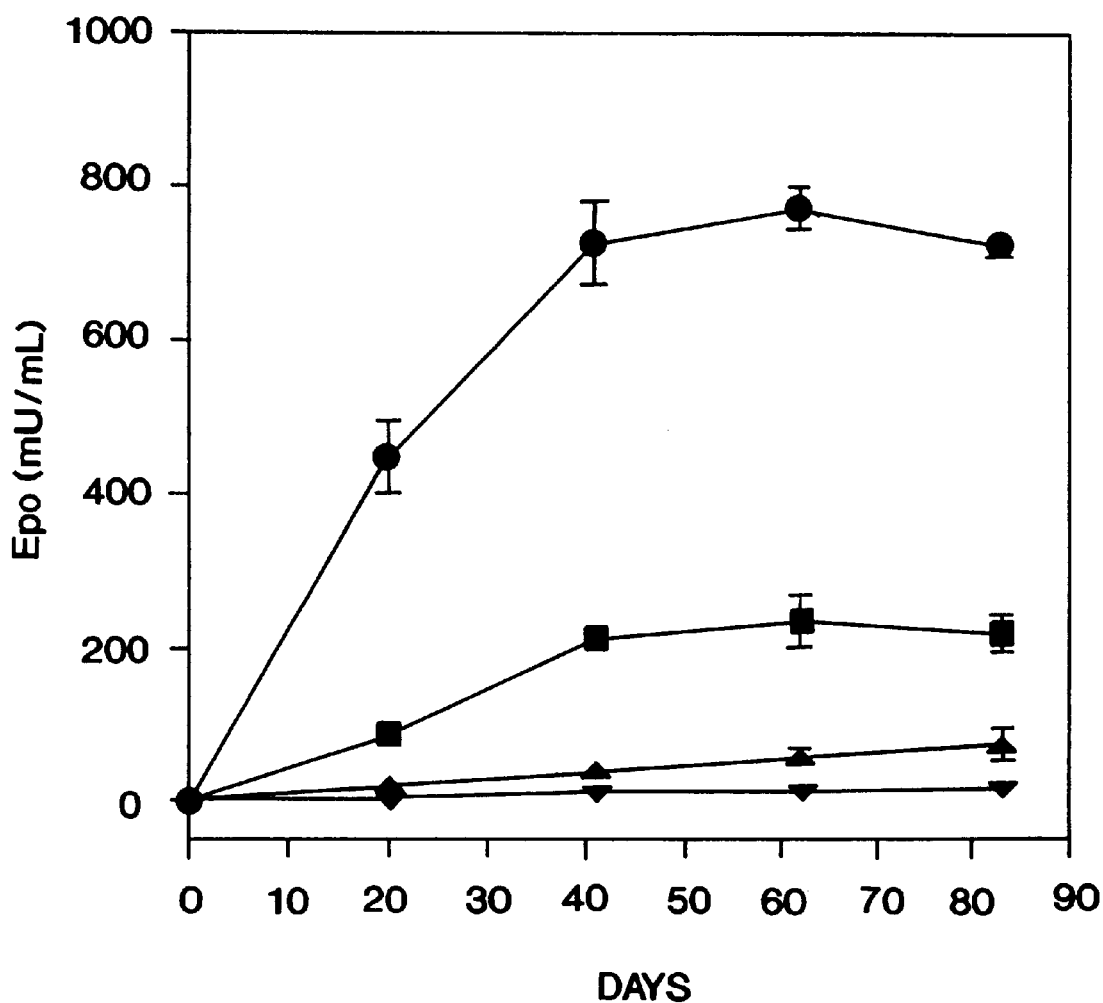
FIG. 7 depicts the time course of EPO secretion in Balb/c mice after IM injection with rAAV-hEPO. Adult Balb/c mice were injected IM with $1 \times 10^{10}$ (▼), $3 \times 10^{10}$ (▲), $1 \times 10^{11}$ (■), or $3 \times 10^{11}$ (●) purified rAAV-LacZ at day=0, and serum EPO levels measured at various time points after injection. Reported values represent means (n=4)±SEM.

The time course of hEPO secretion by animals receiving rAAV-hEPO is depicted in FIG. 7. As can be seen, serum levels of hEPO increased with time to plateau at from 6 to 8 weeks after injection.

The biological activity of secreted hEPO can be monitored by elevation of hematocrit in the experimental animals. A comparison of circulating hEPO levels versus hematocrit is shown in Table II. The comparison shows that hematocrit increased with time and increasing recombinant virion dose. Further, stable elevation in hematocrit has been observed for up to 40 weeks in a group of experimental animals injected with rAAV-hEPO. Control animals had undetectable levels of hEPO (<2.5 mU/mL, the lower limit of detection for the assay).

These results indicate that persistent and stable high-level secretion of hEPO, with a corresponding elevation in hematocrit, is established following a single IM administration of rAAV-hEPO.

In addition, comparison of the expression of hEPO by animals injected IM with rAAV-hEPO ($3 \times 10^{11}$ single-stranded genomes) and animals injected IM with the pW1909EPO plasmid ($1.4 \times 10^{13}$ double-stranded genomes in 100 µg DNA) shows that the recombinant virions gave rise to significantly greater levels of EPO expression. As reported in Table II, 20 days post-injection, recombinant virion-injected animals had serum levels of 445±98 mU/mL, while the plasmid-injected animals had levels of 8±10 mU/mL. At 41 days post-injection, levels in the recombinant virion-treated animals had risen to 725±112 mU/mL, while the levels in the plasmid-treated animals had dropped below the level of detection. The animals receiving rAAV-hEPO exhibited approximately 60-fold more circulating hEPO with 100-fold less input genomes at 20 days post-injection, or approximately 6000-fold greater secretion per genome. At 41 days post-injection, this difference was even greater, since the plasmid expression was below the level of detection.

TABLE II

EPO Expression and Hematocrit: rAAV-hEPO Dose-Response

| | Days after Administration | | | | | | | |
|---|---|---|---|---|---|---|---|---|
| | 20 days | | 41 days | | 62 days | | 83 days | |
| Dose | EPO | HCT | EPO | HCT | EPO | HCT | EPO | HCT |
| $3 \times 10^{11}$ | 445 ± 98 | 74.2 ± 1.2 | 725 ± 112 | 82.3 ± 1.2 | 769 ± 61 | 86.5 ± 1.4 | 723 ± 253 | 88.5 ± 0.7 |
| $1 \times 10^{11}$ | 85 ± 14 | 72.8 ± 1.5 | 212 ± 23 | 79.5 ± 1.7 | 234 ± 75 | 83.2 ± 0.2 | 220 ± 51 | 83.2 ± 2 |
| $3 \times 10^{10}$ | 17 ± 5 | 60.0 ± 3.5 | 34 ± 17 | 74.7 ± 3.2 | 55 ± 28 | 78.7 ± 2.0 | 73 ± 45 | 80.0 ± 3 |
| $1 \times 10^{10}$ | 3 ± 1 | 52.9 ± 1.8 | 11 ± 3 | 61.5 ± 1.9 | 12 ± 8 | 68.4 ± 4.6 | 15 ± 5 | 70.8 ± 8 |
| $3 \times 10^9$ | <2.5 | 49.9 ± 1.4 | <2.5 | 53.5 ± 2.5 | <2.5 | 57.0 ± 2.4 | 4 ± 4 | 57.5 ± 3 |

TABLE II-continued

EPO Expression and Hematocrit: rAAV-hEPO Dose-Response

| | Days after Administration | | | | | | | |
|---|---|---|---|---|---|---|---|---|
| | 20 days | | 41 days | | 62 days | | 83 days | |
| Dose | EPO | HCT | EPO | HCT | EPO | HCT | EPO | HCT |
| i.v. | 7 ± 3 | 54.7 ± 3.2 | 13 ± 2.0 | <64.4 ± 5.3 | 10.1 ± 0.7 | 70.8 ± 8 | 21 ± 10 | 74.6 ± 7 |
| Control | <2.5 | 48.9 ± 1.0 | <2.5 | 49.1 ± 0.8 | <2.5 | 48.1 ± 0.7 | <2.5 | 48.2 ± 9 |
| Plasmid | 8 ± 10 | 50 ± 3.0 | <2.5 | 50.2 ± 1.0 | <2.5 | 47.8 ± 0.9 | N.D. | N.D. |

Values representing means ± standard deviation (SD). EPO = serum levels of human EPO (mU/mL) in Balb/c mice; HCT = hematocrit (%); N.D. = not done; i.v. = intravenous injection with $3 \times 10^{11}$ rAAV-hEPO; Plasmid = injection with 100 µg plasmid DNA ($1.4 \times 10^{13}$ double-stranded plasmid molecules); Control = injection with $3 \times 10^{11}$ particles of rAAV-lacZ.

EXAMPLE 7

A Comparison of hEPO Secretion from rAAV-hEPO Administered by IM or IV Routes

A comparison of the circulating levels of hEPO resulting from IM and IV routes of administration was analyzed to determine which method of gene delivery results in higher levels of systemic hEPO. Balb/c mice were injected with $3 \times 10^{11}$ rAAV-hEPO using either the IM route as described above, or intravenously (IV) in PBS in a total volume of 50 µL via the lateral tail vein. Serum hEPO levels were determined by ELISA using the methods described above.

As shown in Table II, hEPO levels resulting from the IV administrations were significantly lower than the group that received the virions by the IM route. In particular, at 20 days post-injection, the IM route resulted in levels of hEPO of 445±98 mU/mL, while the IV route produced 7±3.0 mU/mL. At 41 days post-injection, the EPO level observed with the IM route was 725±112 as compared with 13±2.0 mU/mL by IV, or it approximately 60-fold more efficacious. These data demonstrate that the IM route of injection resulted in higher systemic levels of hEPO, and suggest that interstitial delivery in muscle results in improved transduction by the recombinant AAV virions.

EXAMPLE 8

In vitro and In vivo Transduction of Muscle Cells Using rAAV-GAA Virions

Cardiomyopathy in infancy is frequently due to inherited metabolic disease. One such metabolic disease, glycogen storage disease type II (Pompe's disease) is an inherited cardiomyopathy caused by a deficiency in the lysosomal enzyme, acid α-glucosidase (GAA). GAA functions to cleave α-1,4 and α-1,6 linkages of lysosomal glycogen to release monosaccharides. Loss of enzyme activity results in accumulation of lysosomal glycogen in striated muscle, and is characterized by lysosomal rupture, contractile apparatus disruption and glycogen infiltration. Currently, no effective treatment is available.

Accordingly, the following studies were carried out to determine whether the recombinant AAV virions of the present invention can be used to obtain long-term expression of GAA in transduced muscle cells.

A. In vitro transduction of human skeletal muscle cells with rAAV-hGAA virions.

Human skeletal myoblasts were seeded in cell culture plates at a density of $2 \times 10^4$ cells/cm$^2$, grown to confluence in appropriate growth media, and then cultured for 14 days in human DM. Differentiation was 9 verified by microscopic examination for multinucleate cells. In vitro transduction was carried out by adding purified rAAV-hGAA virions at an MOI of $2 \times 10^5$ to the cultured myotubes in OptiMEM medium (Gibco BRL). DM was added to the cultures after virion adsorption. Transduced control cultures were established by transducing the myotubes with rAAV-LacZ at the same MOI, and negative controls were established by culturing non-transduced myotubes.

Culture media was changed 24 hours prior to collection of supernatants at day 3, 8 and 14 post transduction. hGAA expression was determined by enzymatic assay. Specifically, cell monolayers were harvested with 0.05% trypsin in Puck's saline A containing 0.02% ethylenediaminetetraacetic acid. After quenching the trypsin with growth media, cells were centrifuged, the cell pellet washed with PBS, and resuspended in distilled water. Following three freeze-thaw cycles, the samples were microfuged at 10,000×g. Protein in the supernatant was determined using the Bicinchoninic acid method (Pierce) with bovine serum albumin (BSA) as the standard. GAA activity was measured using cleavage of the glycogen analog 4-methylumbelliferyl-α-D-glucoside, by a modification of a previously described method (Galjaard et al. (1973) *Clin. Chim. Acta.* 49:361–375; Galjaard, H. (1973) *Pediatr. Res.* 7:56). Assays contained 30 µg protein in 125 µL water. Two volumes of 200 mM sodium acetate (pH 4.3) and 750 nM 4-methyumbelliferyl-α-D-glucoside (from a stock solution of 200 mM in dimethylsulfoxide) were added and the samples incubated at 37° C. for one hour. Reactions were stopped with 625 µL sodium carbonate (pH 10.7). Once cleaved and alkalinized, the 4-methyumbelliferyl fluoresces. Measurements were made with a fluorescence spectrophotometer with excitation at 365 nm and emission at 448 nm. Assay measurements were compared against 4-methyumbelliferone (Sigma, St. Louis, Mo.) standards. Zero protein and zero time blanks were used.

Figure 8:
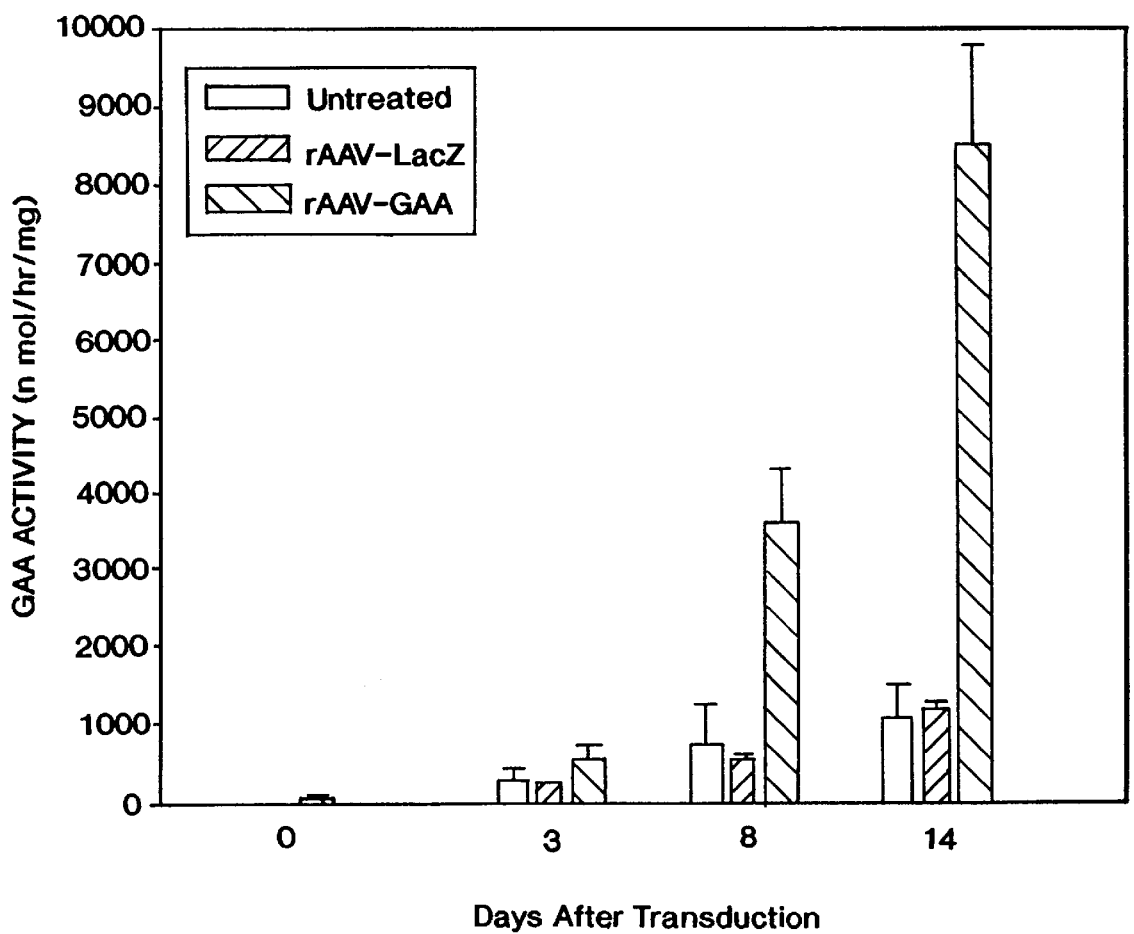
FIG. 8 shows high level expression of acid α-glucosidase (GAA) in human skeletal muscle transduced in vitro with rAAV-hGAA as described in Example 8, Part A. In the study, differentiated human myoblasts were exposed to rAAV-hGAA virions at a MOI of $2 \times 10^5$. Cells were collected at the time points indicated, and GAA activity measured by enzymatic assay. Non-transduced control cells (open bar) and cells transduced with rAAV-LacZ (left cross-hatched bar) showed no significant expression of GAA, while cells transduced with rAAV-hGAA (right cross-hatched bar) showed high levels of GAA activity. The bar graph represents mean GAA activity determined in triplicate cultures±SEM.

The observed GAA activity is reported in FIG. 8 which demonstrates that in vitro transduction of the human myotubes results in high level GAA expression at day 8 and 14 post transduction.

B. In vivo transduction of skeletal muscle using rAAV-GAA virions.

Recombinant AAV virions encoding human GAA were administered to adult Balb/c mice in vivo to determine if systemic levels of GAA can be produced by the transduced cells. Muscle tissue was isolated at various time points after administration, and processed for GAA activity using an enzymatic assay.

In the study, tibialis anterior muscle in Balb/c mice was surgically exposed, and a single intramuscular injection into the left and right muscles (under direct vision) was used to administer the following formulations: phosphate-buffered saline (PBS) alone (negative control); or PBS containing either $2 \times 10^{10}$ rAAV-hGAA or rAAV-LacZ (for a total of $4 \times 10^{10}$ virions/animal).

Figure 9:
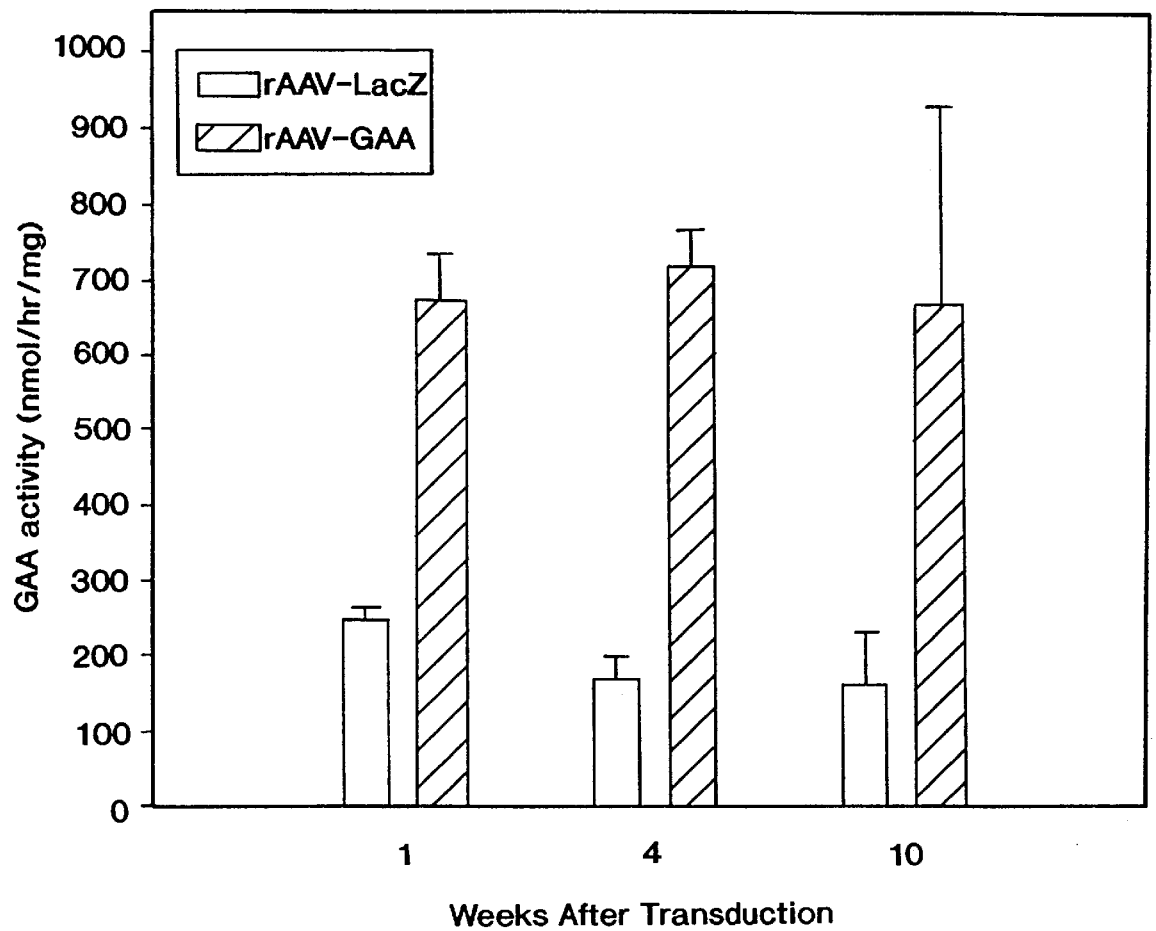
FIG. 9 shows expression of acid α-glucosidase in Balb/c mice tibialis anterior muscle cells that were transduced in vivo with rAAV-hGAA, as described in Example 8, Part B. Adult Balb/c mice were injected intramuscularly (IM) with $4 \times 10^{10}$ rAAV-hGAA (left cross-hatched bar) or the same dose of rAAV-LacZ (open bar). At various time points after injection, muscle tissue was harvested for analysis of GAA activity by enzymatic assay. The bar graph shows mean GAA activity determined in five animals (weeks 1 and 4), or in four animals (week 10)±SEM.

Tissue samples of tibialis anterior muscle were obtained at 1, 4 and 10 weeks following transduction. The tissue samples were prepared by homogenization in water followed by three freeze-thaw cycles. Freeze-thaw lysates were microcentrifuged, and the resultant supernatant assayed for GAA activity as described above. The results of the study are depicted in FIG. 9. As can be seen, stable expression of GAA in the transduced mouse muscle cells was observed for ten weeks, demonstrating that the recombinant AAV virions of the present invention are able to establish efficient expression of a functional lysosomal protein in transduced cells, and thus provide a therapeutic approach for the treatment of glycogen storage disease.

Accordingly, novel methods for transferring genes to muscle cells have been described. Although preferred embodiments of the subject invention have been described in some detail, it is understood that obvious variations can be made without departing from the spirit and the scope of the invention as defined by the appended claims.

Deposits of Strains Useful in Practicing the Invention

A deposit of biologically pure cultures of the following strain was made with the American Type Culture Collection, 12301 Parklawn Drive, Rockville, Md., under the provisions of the Budapest Treaty. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

This deposit is provided merely as a convenience to those of skill in the art, and is not an admission that a deposit is required. A license may be required to make, use, or sell the deposited materials, and no such license is hereby granted.

| Strain | Deposit Date | ATCC No. |
|---|---|---|
| pGN1909 | July 20, 1995 | 69871 |

We claim:

1. An adeno-associated virus (AAV) vector comprising a gene encoding a lysosomal enzyme operably linked to transcriptional and translational control elements.

2. The AAV vector of claim 1, wherein said gene encodes acid α-glucosidase.

3. A recombinant adeno-associated virus (AAV) virion which comprises the AAV vector of claim 2.

4. A composition comprising recombinant AAV virions according to claim 3 and an acceptable excipient.

5. A recombinant adeno-associated virus (AAV) virion which comprises the AAV vector of claim 1.

6. A composition comprising recombinant AAV virions according to claim 5 and an acceptable excipient.

* * * * *